(12) United States Patent
Kuo et al.

(10) Patent No.: US 8,900,555 B2
(45) Date of Patent: Dec. 2, 2014

(54) INSULIN DERIVATIVE FORMULATIONS FOR PULMONARY DELIVERY

(75) Inventors: Mei-Chang Kuo, Palo Alto, CA (US); Michael Eldon, Redwood City, CA (US); Yiqiong Yuan, Alameda, CA (US)

(73) Assignee: Nektar Therapeutics, San Francisco, CA (US)

(*) Notice: Subject to any disclaimer, the term of this patent is extended or adjusted under 35 U.S.C. 154(b) by 1214 days.

(21) Appl. No.: 12/374,891

(22) PCT Filed: Jul. 27, 2007

(86) PCT No.: PCT/US2007/016903
§ 371 (c)(1), (2), (4) Date: Nov. 11, 2009

(87) PCT Pub. No.: WO2008/013938
PCT Pub. Date: Jan. 31, 2008

(65) Prior Publication Data
US 2010/0055049 A1 Mar. 4, 2010

Related U.S. Application Data

(60) Provisional application No. 60/833,731, filed on Jul. 27, 2006.

(51) Int. Cl.
- *A61K 9/12* (2006.01)
- *A61K 9/00* (2006.01)
- *A61K 38/28* (2006.01)

(52) U.S. Cl.
CPC ............... *A61K 9/0073* (2013.01); *A61K 38/28* (2013.01)
USPC ................................................. 424/45

(58) Field of Classification Search
USPC ................................................. 424/45
See application file for complete search history.

(56) References Cited

U.S. PATENT DOCUMENTS

2004/0247870 A1* 12/2004 Brown et al. ................. 428/402
2006/0222698 A1* 10/2006 Lau et al. ..................... 424/450

FOREIGN PATENT DOCUMENTS

| WO | WO 02/078675 | 10/2002 |
| WO | WO 2005/067898 | 7/2005 |
| WO | WO 2008/013955 | 1/2008 |

OTHER PUBLICATIONS

Novak et al, New Trends in Insulin Therapy, 2003, Diabetologia Croatica, 32-2, pp. 55-63.*
Tanaka et al, Effect of Structural Relaxation on the Physical and Aerosol Properties of Amorphous Form of FK888(NK1 Antagonist), 2005, Chem. Pharm. Bull., 51 (5), pp. 498-502.*
Grainger et al, Administration of an insulin powder to the lungs of cynomolgus monkeys using a Penn Century insufflator, 2004, International Journal of Pharmaceutics, 269, pp. 523-527.*
Adis International, Insulin inhalation—Pfizer/Nektar Therapeutics: HMR 4006, inhaled PEG-insulin—Nektar, PEGylated insulin—Nektar, Drugs in R&D, vol. 5, No. 3, pp. 166-170)5) (2004).

* cited by examiner

*Primary Examiner* — Trevor Love
(74) *Attorney, Agent, or Firm* — Mark A. Wilson

(57) ABSTRACT

Aerosolizable formulations comprising: an insulin derivative having an isoelectric point (pI) ranging from about 6 to about 8; and a pharmaceutically acceptable excipient including a precipitating agent.

3 Claims, 9 Drawing Sheets

US 8,900,555 B2

INSULIN DERIVATIVE FORMULATIONS FOR PULMONARY DELIVERY

This application claims benefit of U.S. Provisional Application 60/833,731, filed Jul. 27, 2006, the contents of the above application is incorporated herein in its entirety.

FIELD OF THE INVENTION

The present invention relates to pharmaceutical formulations and related methods. For example, in one or more embodiments, the present invention relates to formulations for pulmonary delivery, including sustained release formulations. Formulations of the invention may include an insulin derivative, such as glargine insulin, and a pharmaceutically acceptable excipient, such as a precipitating agent. In some embodiments, the present invention includes glargine insulin and a divalent cation as the precipitating agent. In one or more embodiments, the formulations can become soluble, and then precipitate, upon reaching the deep lung.

BACKGROUND OF THE INVENTION

Administration of pharmaceutical formulations of peptides traditionally has been performed by injection, thereby avoiding drug degradation by the gastrointestinal tract. Injection, however, is generally regarded as being less than desirable, because of the immediate discomfort at the injection site, as well as because of long-term tissue damage that can be caused by repeated injections to a common area. Besides injection, other routes of administration include transdermal, intranasal, intratracheal, and pulmonary delivery.

Delivery of therapeutics through pulmonary routes is particularly advantageous. This approach eliminates the need for needles, limits irritation to the skin and body mucosa (common side effects of transdermally, iontophoretically, and intranasally delivered drugs), and eliminates the need for nasal and skin penetration enhancers (typical components of intranasal and transdermal systems that often cause skin or membrane irritations/dermatitis). Pulmonary administration is also economically attractive, amenable to patient self-administration, and is often preferred by patients over other alternative modes of administration.

However, pulmonary administration poses a number of difficulties that are not encountered in other routes of administration. For example, whereas intranasal or transdermal administration involves placing the drug to be absorbed in immediate or very close proximity to the actual point of absorption, pulmonary administration requires administering the drug several feet away from the actual point of absorption. Thus, a pulmonary formulation must survive a relatively long journey through the mouth, down the trachea, and into the lungs. If not properly formulated and delivered, the drug will not reach the site of absorption in the distal lungs, and availability is compromised.

The problems become even more complicated when a controlled or delayed release of the pulmonarily delivered drug is desired. A number of methods have been employed to control the release rate of drugs from pulmonary pharmaceutical compositions (see, e.g., Zeng, X. M., et al., "The controlled delivery of drugs to the lung," Int. J. Pharmaceutics 124, 149-164 (1995)). Examples of these methods include, for example, the use of liposomes or biodegradable microspheres, and modification of the drug so that the active form of the drug is not readily released. Another method is to include the drug in an insoluble complex. For example, the injectable sustained release insulin formulations often contain insulin in a crystallized form, which releases insulin more slowly than compositions comprising free insulin. The insulin crystals that exhibit a satisfactory sustained release profile in injectable compositions, however, are not suitable for pulmonary delivery, because the crystals are too large and deposit prematurely before they reach the deep lung.

Glargine insulin, or insulin glargine, is an insulin analog that substitutes asparagine 21 of insulin with glycine, and adds two arginine residues to the C-terminus of the B chain of insulin. The molecular modification shifts the isoelectric point from pH 5.4 of insulin to pH 6.7 of glargine, and stabilizes the glargine hexamer. Therefore, at pH 4.0, insulin glargine is a clear, soluble solution. When insulin glargine is injected into tissue having physiological pH, the resulting change in pH causes the drug to precipitate. The formation of the precipitate, along with the increased stabilization of the insulin glargine hexamer, as well as inter-hexamer interaction, retards the absorption after injection, thereby resulting in a prolonged plasma level.

U.S. Published Application No. 2005/0084537, which is incorporated herein by reference in its entirety, discloses microparticles comprising a therapeutic agent, e.g., glargine, dispersed within a polymer matrix. The matrix comprises a first polymer of hyaluronic acid and a second polymer of either a non-ionic polymer, a polymeric gum, or a combination thereof. The microparticles may be formulated for nasal or pulmonary delivery.

Because of its unique physicochemical properties, glargine insulin presents additional challenges to formulating for pulmonary administration. The present invention is thus directed to the preparation of a formulation for pulmonary administration comprising insulin derivatives.

SUMMARY OF THE INVENTION

The present invention provides, in some embodiments, aerosolizable formulations, comprising: an insulin derivative having an isoelectric point (pI) ranging from about 6.0 to about 8.0; and at least one pharmaceutically acceptable excipient; wherein the at least one pharmaceutically acceptable excipient comprises a precipitating agent.

In some embodiments, the invention provides methods for preparing an aerosol formulation, comprising: preparing a solution comprising an insulin derivative having an isoelectric point (pI) of from about 6 to about 8, and a pharmaceutically acceptable excipient; and adding a pharmaceutically acceptable buffer to achieve a pH of the solution from about 3 to about 6.

In some embodiments, the invention provides methods of reducing blood glucose level in a mammal, comprising: pulmonarily administering to the mammal a pharmaceutical formulation comprising particles of an insulin derivative having an isoelectric point of from about 6 to about 8, and at least one pharmaceutically acceptable excipient; wherein the insulin derivative precipitates upon deposition in the lungs of the mammal, and wherein administration results in a reduction in blood glucose level for a period of at least about 6 hours.

The invention also provides, in some embodiments, methods of reducing blood glucose level in a mammal, comprising: pulmonarily administering to the mammal a pharmaceutical formulation for inhalation, the formulation comprising a solution of an insulin derivative having an isoelectric point of from about 6 to about 8, and at least one precipitating agent; wherein at least some of the insulin derivative precipitates upon contact with lung tissue, and at least some of the insulin derivative is absorbed to result in an initial reduction in blood glucose level, wherein the precipitated insulin derivative is absorbed over a period of at least about 6 hours; and wherein the method results in a maintained reduction in blood glucose level for at least about 6 hours.

Also provided by this invention are, in some embodiments, methods of reducing blood glucose level in a mammal, comprising: pulmonarily administering to the mammal a pharmaceutical formulation comprising particles comprising precipitated insulin derivative having an isoelectric point of from about 6 to about 8, and at least one pharmaceutically acceptable excipient; wherein administration results in a reduction in blood glucose level for a period of at least about 6 hours.

Still further, the invention provides, in some embodiments, pharmaceutical formulations for inhalation, comprising particles having a mass median aerodynamic diameter of less than 10 μm, comprising glargine insulin, zinc, leucine, and trehalose.

Other features and advantages of the present invention will be set forth in the description of invention that follows, and will be apparent, in part, from the description or may be learned by practice of the invention. The invention will be realized and attained by the devices and methods particularly pointed out in the written description and claims hereof.

BRIEF DESCRIPTION OF THE DRAWINGS

The present invention is further described in the description of invention that follows, in reference to the noted plurality of non-limiting drawings, wherein.

DETAILED DESCRIPTION OF THE INVENTION

Figure 1:
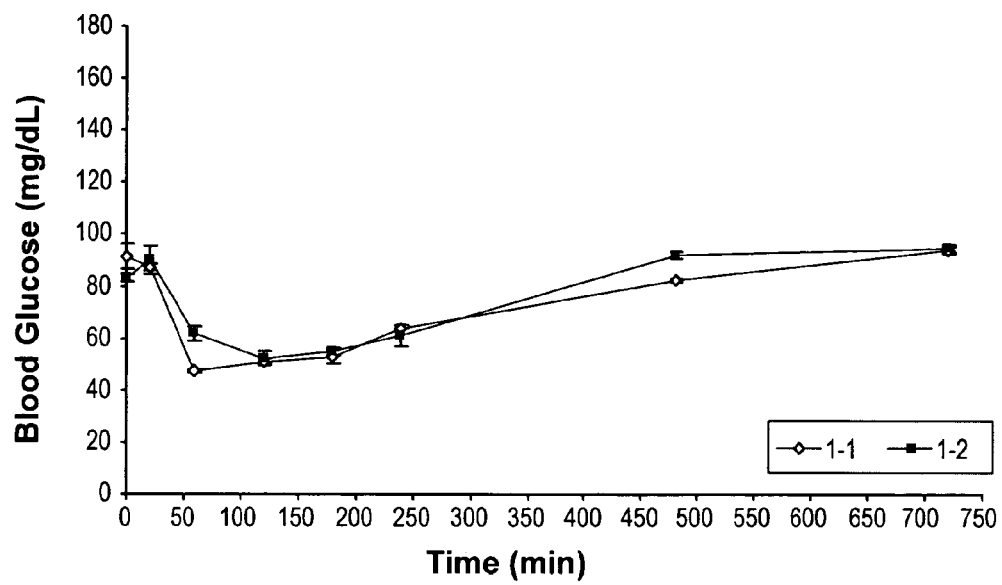
FIG. 1 is a graph showing individual blood glucose concentrations following 80 μg intratracheal instillation of insulin glargine to Sprague-Dawley rats (n=2). Error bars are standard deviation.
Figure 2:
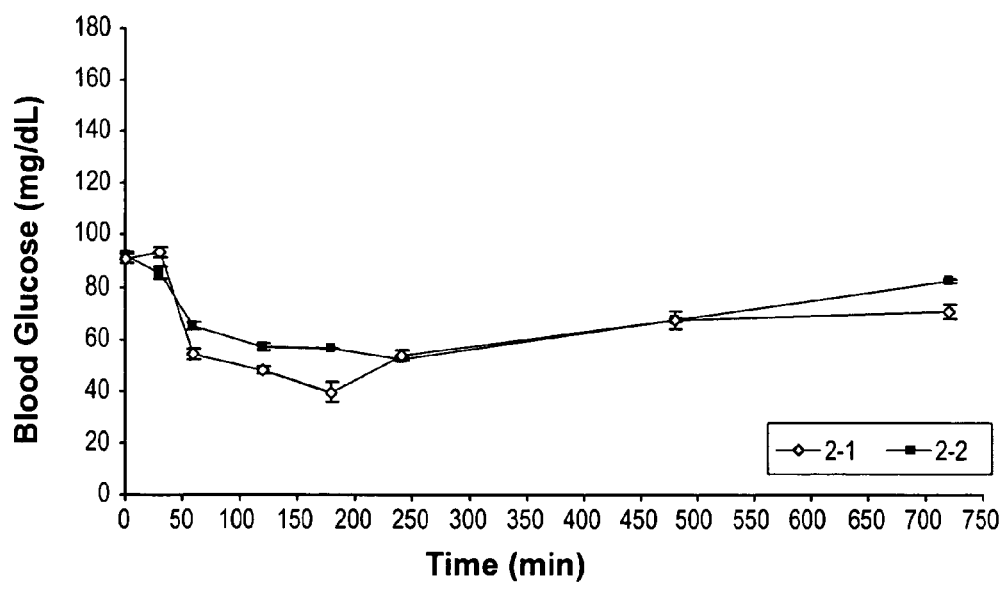
FIG. 2 is a graph showing individual blood glucose concentrations following 160 μg intratracheal instillation of insulin glargine to Sprague-Dawley rats (n=2). Error bars are standard deviation.
Figure 3:
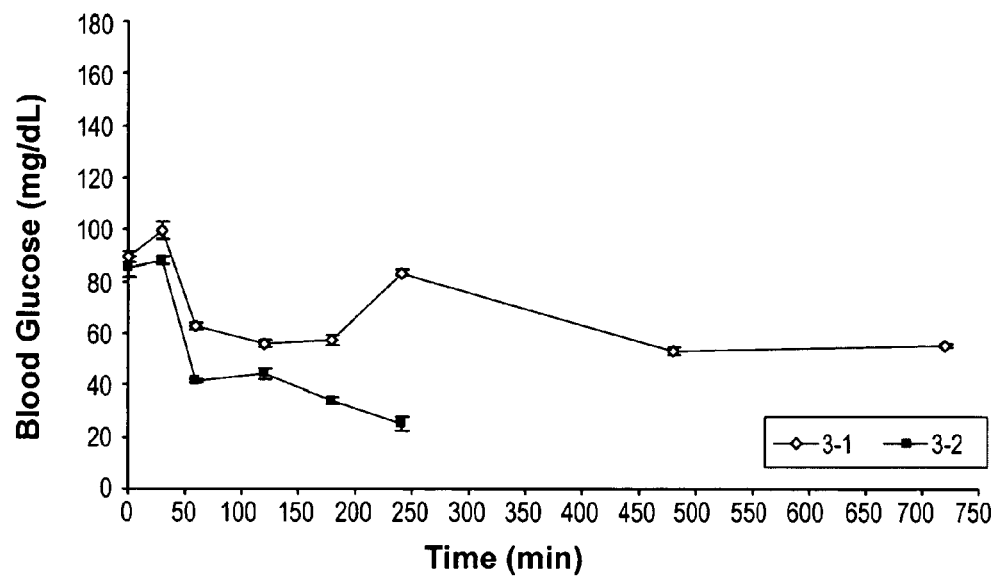
FIG. 3 is a graph showing individual blood glucose concentrations following 320 μg intratracheal instillation of insulin glargine to Sprague-Dawley rats (n=2). Error bars are standard deviation. Animal 3-2 was euthanized after 240 min post-dose due to hypoglycemia.
Figure 4:
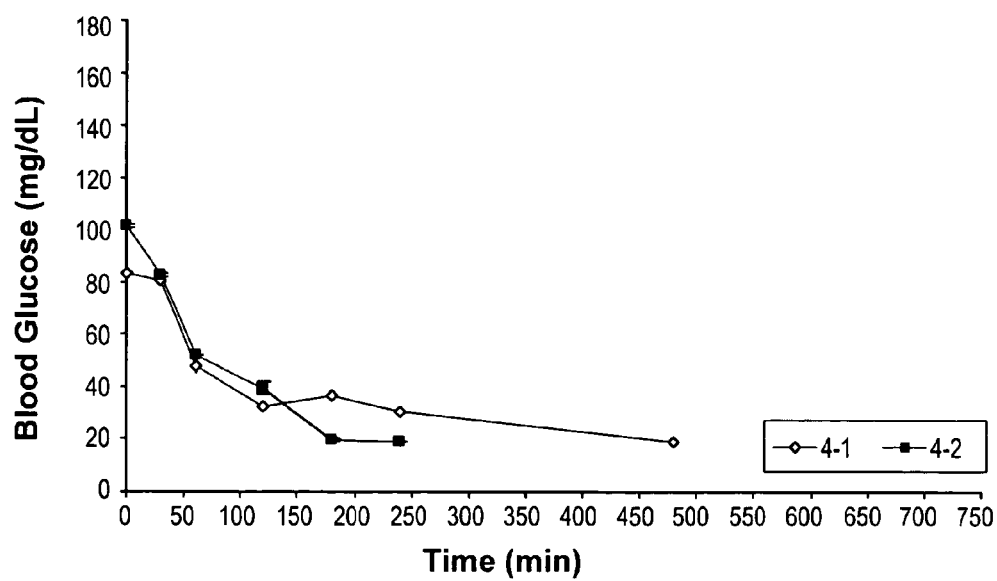
FIG. 4 is a graph showing individual blood glucose concentrations following 640 μg intratracheal instillation of insulin glargine to Sprague-Dawley rats (n=2). Error bars are standard deviation. Animal 4-1 was euthanized after 480 min post-dose due to hypoglycemia and Animal 4-2 was euthanized after 240 min post-dose due to hypoglycemia.
Figure 5:
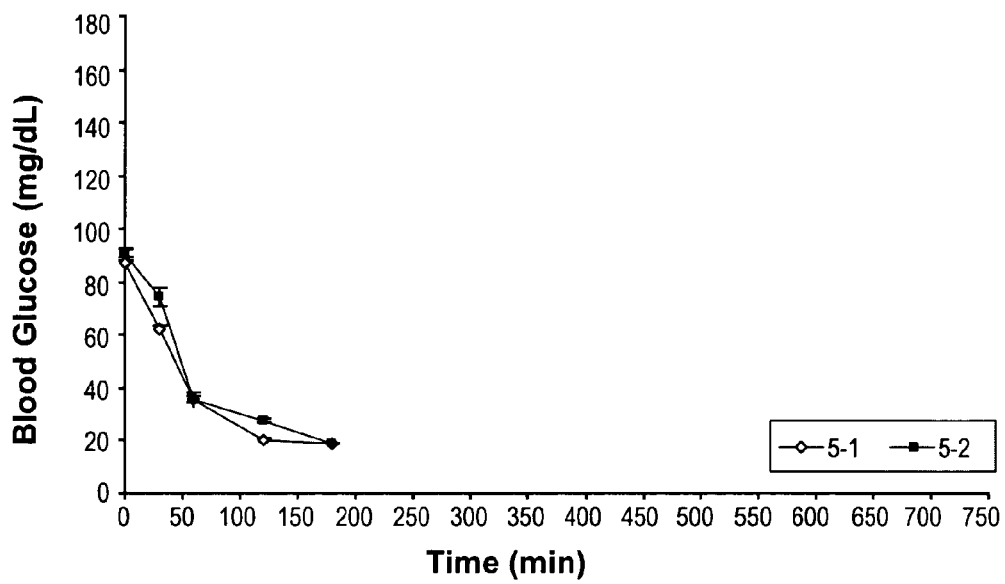
FIG. 5 is a graph showing individual blood glucose concentrations following 960 μg intratracheal instillation of insulin glargine to Sprague-Dawley rats (n=2). Error bars are standard deviation. Animals 5-1 and 5-2 were euthanized after 180 min post-dose due to hypoglycemia.

Unless otherwise stated, a reference to a compound or component includes the compound or component by itself, as well as in combination with other compounds or components, such as mixtures of compounds.

As used herein, the singular forms "a," "an," and "the" include the plural reference unless the context clearly dictates otherwise.

Except where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not to be considered as an attempt to limit the application of the doctrine of equivalents to the scope of the claims, each numerical parameter should be construed in light of the number of significant digits and ordinary rounding conventions.

Additionally, the recitation of numerical ranges within this specification is considered to be a disclosure of all numerical values and ranges within that range. For example, if a range is from about 1 to about 50, it is deemed to include, for example, 1, 7, 34, 46.1, 23.7, or any other value or range within the range.

Before further discussion, a definition of the following terms will aid in the understanding of the present invention.

DEFINITIONS

The terms used in this disclosure are defined as follows unless otherwise indicated. Standard terms are to be given their ordinary and customary meaning as understood by those of ordinary skill in the art, unless expressly defined herein.

"Amino acid" refers to any compound containing both an amino group and a carboxylic acid group. Although the amino group most commonly occurs at the position adjacent to the carboxy function (α-position), the amino group may be positioned at any location within the molecule. The amino acid may also contain additional functional groups, such as amino, hydroxyl, thio, carboxyl, carboxamide, imidazole, etc. An amino acid may be synthetic or naturally occurring, and may be used in either its racemic or optically active (D-, or L-) form.

"Leucine," whether present as a single amino acid or as an amino acid component of a peptide, refers to the amino acid leucine, which may be a racemic mixture or in either its D- or L-form, as well as modified forms of leucine (i.e., where one or more atoms of leucine have been substituted with another atom or functional group) in which the dispersibility-enhancing effect of the modified amino acid or peptide is substantially unchanged or unimproved over that of the unmodified material.

"Dipeptide," also referred to herein as a dimer, refers to a peptide including two amino acids.

"Tripeptide," also referred to herein as a trimer, refers to a peptide including three amino acids.

A "surface active" material is one having surface activity (measured, e.g., by surface tensiometry), as characterized by its ability to reduce the surface tension of the liquid in which it is dissolved. Surface tension, which is associated with the interface between a liquid and another phase, is that property of a liquid by virtue of which the surface molecules exhibit an inward attraction.

Typically, in the context of the present invention, a surface active dipeptide or tripeptide is identified by preparing solutions of varying concentrations (for example, from approximately 0.01% wt/vol (0.1 mg/ml) to approximately 2% wt/vol (20 mg/ml)) of the subject peptide in water, and measuring the surface tension of each of the solutions. A surface-active peptide is one that, when present at any concentration in solution, though typically present in an amount greater than 0.25 mg/ml, is effective to lower the surface tension of water from its control value. A peptide that is more surface-active than another peptide is one that decreases the surface tension of water to a greater extent, when present in the liquid at the same concentration and measured under the same set of experimental conditions.

A "sustained release composition" is a composition that releases the active component slowly over a relatively longer period of time than an "immediate release" composition. In general, the active component is released over at least about 3 hours, or at least about 4 hours, or at least about 5 hours, or at least about 6 hours, or at least about 8 hours.

A substance is "amorphous" if particles of the substance possess no uniform shapes. For example, a crystal substance is not amorphous.

A "protein" is an organic compound comprising one or more chains of amino acid residues linked by peptide bonds. As used herein, the term "protein" encompasses proteins of any length and derivatives thereof, such as peptides, glycopeptides, lipopeptides, glycoproteins, and lipoproteins. These terms may be used interchangeably herein.

A "pharmaceutical protein" is a protein useful for pharmaceutical purposes.

By "insulin derivative" as used herein is meant a naturally occurring insulin or an insulin analogue which has been chemically modified, e.g. by introducing a side chain in one or more positions of the insulin backbone or by oxidizing or reducing groups of the amino acid residues in the insulin or by converting a free carboxylic group to an ester group or to an amide group. Derivatives include those obtained by acylating a free amino group or a hydroxy group. Derivatives also include those in which one or more amino acids (e.g., 1, 2, 3, 4, 5, or more) have been deleted and/or replaced by other amino acids, including non-codeable amino acids, and those comprising additional amino acids, i.e. more than 51 amino acids (e.g., 1, 2, 3, 4, 5, or more), such that the resulting derivative possesses insulin activity.

A "sustained plasma level" of a protein for a specified period of time means that the protein can be detected in the plasma for a duration specified. A protein can be detected by any methods for detecting such protein, e.g., immunological, biochemical, or functional methods. For example, glargine insulin can be detected by enzyme-linked immunosorbent assay (ELISA), mass spectrometry, or determination of blood glucose levels.

A "precipitating agent" is a chemical compound or mixture of chemical compounds that is capable of precipitating a protein of interest when the agent is added to an aqueous solution of the protein. A protein can be precipitated by a variety of mechanisms, including but not limited to, affinity precipitation, salting out, and isoelectric precipitation.

An "insoluble complex" is a complex that does not completely dissolve in an excess of water, or a designated solvent, where specified, in an hour at 37° C. Typically, an insoluble complex has a solubility of less than about 30%, i.e., less than about 30% of the complex is dissolved in an hour. The insoluble complex can have a solubility of less than about 20%, or less than about 10%, or less than about 5%.

A composition that is "suitable for pulmonary delivery" refers to a composition that is capable of being aerosolized and inhaled by a subject so that a portion of the aerosolized particles reaches the lungs to permit penetration into the alveoli. Such a composition may be considered "respirable" or "inhaleable."

An "aerosolized" composition contains liquid or solid particles that are suspended in a gas (typically air), typically as a result of actuation (or firing) of an inhalation device such as a dry powder inhaler, an atomizer, a metered dose inhaler, or a nebulizer.

A "jet nebulizer" is a system, such as a device, that forces compressed air through a solution of a drug so that a fine spray can be delivered to a facemask and inhaled. Nebulizers often are used to administer drugs to those who lack the ability to use a metered-dose or breath-activated inhaler.

A "dry powder inhaler" is a device that is loaded with a unit dose of the drug in powder form. Generally, the inhaler is activated by taking a breath. For example, a capsule or blister is punctured and the powder is dispersed so that it can be inhaled, e.g., in a "Spinhaler" or "Rotahaler." "Turbohalers" are fitted with canisters that deliver measured doses of the drug in powder form.

A "metered dose inhale" or "MDI" is a device that delivers a measured dose of a drug in the form of a suspension of extremely small liquid or solid particles, which is dispensed from the inhaler by a propellant under pressure. Such inhalers are placed into the mouth and depressed (activated) to release the drug as the individual takes a breath.

As used herein, the term "emitted dose" or "ED" refers to an indication of the delivery of dry powder from an inhaler device after an actuation or dispersion event from a powder unit or reservoir. ED is defined as the ratio of the dose delivered by an inhaler device to the nominal dose (i.e., the mass of powder per unit dose placed into a suitable inhaler device prior to firing). The ED is an experimentally determined amount, and may be determined using an in vitro device set up which mimics patient dosing. To determine an ED value, as used herein, dry powder is placed into a Pulmonary Delivery System (PDS) device (Nektar Therapeutics), described in U.S. Pat. No. 6,257,233, which is incorporated herein by reference in its entirety. The PDS device is actuated, dispersing the powder. The resulting aerosol cloud is then drawn from the device by vacuum (30 L/min) for 2.5 seconds after actuation, where it is captured on a tared glass fiber filter (Gelman, 47 mm diameter) attached to the device mouthpiece. The amount of powder that reaches the filter constitutes the delivered dose. For example, for a capsule containing 5 mg of dry powder that is placed into an inhalation device, if dispersion of the powder results in the recovery of 4 mg of powder on a tared filter as described above, then the ED for the dry powder composition is 80% (=4 mg (delivered dose)/5 mg (nominal dose)).

A composition in "dry powder form" is a powder composition that typically contains less than about 20% moisture.

As used herein, "mass median diameter" or "MMD" refers to the median diameter of a plurality of particles, typically in a polydisperse particle population, i.e., consisting of a range of particle sizes. MMD values as reported herein are determined by laser diffraction (Sympatec Helos, Clausthal-Zellerfeld, Germany), unless the context indicates otherwise. Typically, powder samples are added directly to the feeder funnel of the Sympatec RODOS dry powder dispersion unit. This can be achieved manually or by agitating mechanically from the end of a VIBRI vibratory feeder element. Samples are dispersed to primary particles via application of pressurized air (2 to 3 bar), with vacuum depression (suction) maximized for a given dispersion pressure. Dispersed particles are probed with a 632.8 nm laser beam that intersects the dispersed particles' trajectory at right angles. Laser light scattered from the ensemble of particles is imaged onto a concentric array of photomultiplier detector elements using a reverse-Fourier lens assembly. Scattered light is acquired in time-slices of 5 ms. Particle size distributions are back-calculated from the scattered light spatial/intensity distribution using an algorithm.

"Mass median aerodynamic diameter," or "MMAD," is a measure of the aerodynamic size of a dispersed particle. The aerodynamic diameter is used to describe an aerosolized powder in terms of its settling behavior, and is the diameter of a unit density sphere having the same settling velocity, in air, as the particle. The aerodynamic diameter encompasses particle shape, density, and physical size of a particle. As used herein, MMAD refers to the midpoint or median of the aerodynamic particle size distribution of an aerosolized powder determined by cascade impaction at standard conditions using a Pulmonary Delivery System (PDS) device (Nektar Therapeutics), described in U.S. Pat. No. 6,257,233, which is incorporated herein by reference in its entirety, unless otherwise indicated.

"Fine particle fraction" is the fraction of particles with an aerodynamic diameter that is less than 5 microns (μm). Where specified, the fine particle fraction may also refer to the fraction of particles with an aerodynamic diameter that is less than 3.3 microns.

A "pharmaceutically acceptable excipient or carrier" refers to an excipient that may optionally be included in the compositions of the present invention. Preferred are excipients that can be taken into the lungs with no significant adverse toxicological effects to the subject, particularly to the lungs of the subject.

"Glass transition temperature (Tg)", as used herein, is the onset of a temperature range at which a composition changes from a glassy or vitreous state to a syrup or rubbery state. Generally, Tg is determined using differential scanning calorimetry (DSC). The standard designation for Tg is the temperature at which onset of the change of heat capacity (Cp) of the composition occurs upon scanning through the transition. The definition of Tg, however, can be arbitrarily defined as the onset, midpoint or endpoint of the transition. For purposes of the present invention, we will use the onset of the changes in Cp when using DSC. See the article entitled "Formation of Glasses from Liquids and Biopolymers" by C. A. Angell: Science, 267, 1924-1935 (Mar. 31, 1995) and the article entitled "Differential Scanning Calorimetry Analysis of Glass Transitions" by Jan P. Wolanczyk: Cryo-Letters, 10, 73-76 (1989). For detailed mathematical treatment, see "Nature of the Glass Transition and the Glassy State" by Gibbs and DiMarzio: Journal of Chemical Physics, 28, No. 3, 373-383 (March, 1958). These articles are incorporated herein by reference.

A "glass-forming excipient" is an excipient that, when added to a composition, promotes glassy state formation of the composition.

The term "glass" or "glassy state," as used herein, refers to a liquid that has lost its ability to flow, i.e. it is a liquid with a very high viscosity, wherein the viscosity ranges from $10^{10}$ to $10^{14}$ pascal-seconds. It can be viewed as a metastable amorphous system in which the molecules have vibrational motion and reduced rotational motion, but have very slow (almost immeasurable) translational motion when compared to the liquid state. As a metastable system, it is stable for long periods of time when stored well below the glass transition temperature. Because glasses are not in a state of thermodynamic equilibrium, glasses stored at temperatures at or near the glass transition temperature relax to equilibrium upon storage and lose their high viscosity. The resultant rubbery or syrupy flowing liquid can lead to physical instability of the product. A solvent evaporation technique (U.S. Pat. No. 6,309,671) can be used to achieve a glassy state, as well as other processes that can produce a glassy state with acceptable Tg, for example, freeze drying followed by milling for micronization.

"Treating or ameliorating" a disease or medical condition means reducing or eliminating the symptoms of the disease or medical condition. In some embodiments, "treating or ameliorating" a disease or medical condition will be directed at addressing the cause of the disease or medical condition. Treating a disease may result in cure of the disease.

The term "diabetes and related conditions" refers to diseases or medical conditions caused by the lack or inaction of, or inability to utilize, insulin. Diabetes and related conditions include type I and type II diabetes, particularly type I diabetes.

A "pharmacologically effective amount" or "physiologically effective amount" of a pharmaceutical composition is an amount sufficient for the intended purpose of the pharmaceutical composition. For example, an effective amount of a pharmaceutical composition to treat or ameliorate diabetes is an amount sufficient to reduce or eliminate the symptoms of diabetes, for example, an amount that is needed to provide a desired level of insulin derivative in the bloodstream to result in reduced blood glucose. The pharmacologically effective amount of a given pharmaceutical composition will vary with factors such as the nature of the active component in the composition, the route of administration, the size and species of the animal to receive the composition, and the purpose of the administration. The suitable amount can be readily determined by one skilled in the art based upon available literature and the information provided herein.

Formulations of the Present Invention

In some embodiments, formulations of a pharmaceutically active molecule, such as a peptide or protein, are prepared to be absorbed through lung tissue. The isoelectric point of a peptide or protein is the pH at which this molecule carries no net electrical charge. An accompanying phenomenon of this property is that peptides and proteins generally have their lowest solubility at a pH equal to their pI. At a pH below or above their pI, solubility increases as the peptide or protein carries more charges, which facilitates solvation. Consequently, a dissolved peptide or protein can precipitate when the pH of its environment changes to its pI. Thus, a protein with a pI approximately equal to physiological pH will generally precipitate in or on a tissue when administered from, for example, an acidic solution, and thereby form a depot for protracted dissolution and absorption.

Generally, many proteins are soluble at physiological pH. However, when modified, the pI of the proteins can be manipulated to fall into the range of the physiological pH and thus result in a desired precipitation for protracted dissolution. In one or more embodiments, such manipulation can be done by point mutations of the protein, where one, two, or a few more amino acids of the protein sequence are exchanged to carry residues that trigger the pI into the desired range. In one or more embodiments, insulin or insulin derivative can be tagged with another peptide that carries sufficient residues to change the pI of the complete macromolecule into the desired pH range. In one or more embodiments, residues of insulin or insulin derivative can be chemically modified to change the pI. For example, a negatively charged acidic residue, e.g. glutamate or aspartate, can be modified into a neutral ester. Likewise, a positively charged amine group in a residue such as lysine can form a neutral amide upon treatment with an organic acid. Also, a solution containing a protein of interest can be treated with an agent that facilitates precipitation. Such a precipitation agent may manipulate other factors than the net charge of the protein in solution. For example, a precipitation agent can change the polarity of the solution, or the tertiary or quaternary structure of the protein resulting in an accelerated precipitation. Thus, the manipulation of a protein to gain a pI similar to physiological pH can be used to produce precipitation of this protein at physiological pH, which can be used to provide efficacy over extended time.

It is also expressly contemplated that a protein can be precipitated by bringing the environmental pH to approximate its pI, or by any other means, prepared as a solid, and be administered as a solid into the pulmonary cavity. Such formulation can take the form of, for example, liquid suspensions or dry powders formed from such suspensions, containing the insulin derivative in its precipitated form.

Glargine insulin, or insulin glargine, is an insulin analog that substitutes asparagine 21 of insulin with glycine, and adds two arginine residues to the C-terminus of the B chain of insulin. The molecular modification shifts the isoelectric point from pH 5.4 of insulin to pH 6.7 of glargine, and stabilizes the glargine hexamer. Therefore, at pH 4.0, insulin glargine is a clear, soluble solution. When insulin glargine is injected into tissue having physiological pH, the resulting change in pH causes the drug to precipitate. The formation of the precipitate, along with the increased stabilization of the insulin glargine hexamer, as well as inter-hexamer interaction, retards the absorption after injection, thereby resulting in a prolonged plasma level.

Some embodiments of this invention are directed to pulmonary formulations of glargine insulin that initially are soluble or in solution. Upon reaching the deep lung, as a result of the pH change, the glargine insulin precipitates to form sustained-release complexes. The choice of components in the present formulations is made to maximize both initial solubility, followed by particulate formation. Without wishing to be bound by any particular theory of operations, the formulations of the present invention are believed to, upon reaching the distal lung, become initially soluble to some extent, followed by the formation of precipitates and/or complexes. Thus, in some embodiments, the formulation is a liquid formulation, e.g., a low pH formulation, which can include a solution of the glargine insulin, and in some embodiments, the formulation is a dry powder, which can include a soluble formulation of glargine insulin.

Also, as expressly noted above, glargine insulin, or other proteins within the scope of the invention, which can be precipitated, may be precipitated prior to administration. Such formulations could take the form of a suspension of precipitated glargine insulin, or a dry powder formulation formed therefrom.

It should be noted that reference is made to glargine insulin throughout this specification, but the teachings herein are equally applicable to any insulin derivative having an isoelectric point of about 6-8. Such insulin derivatives can be prepared, for example, by modifying their pI by the replacement of acidic residue 21 with a non-acidic residue, and/or by the addition of basic residues, such as lysine, to a terminus. Modifications of insulin in such manner as to modify its pI without adversely affecting its biological activity are considered routine and well within the level of ordinary skill in the art. Thus, any such insulin derivative or equivalent is contemplated and deemed within the scope of this invention.

Precipitation of the Protein in the Lung

Crystal structure analysis has revealed that insulin forms a complex with a suitable agent such as a precipitating agent such as zinc at a ratio of two or four zinc molecules to each insulin hexamer. The glargine insulin-zinc complexes in some embodiments of the present invention, however, may contain more zinc and form amorphous, rather than crystalline, complexes. Without wishing to be limited to a theory, it appears that the high levels of zinc (or other precipitating agents) in the compositions of the present invention lead to the formation of "kinetically irreversible precipitates," which dissociate much more slowly than the insulin-zinc crystals described above. The term "kinetically irreversible" does not mean that the precipitation process is not reversible. Rather, it means that dissociation, with subsequent dissolution, is a slow process that is kinetically controlled.

The formation of the "kinetically irreversible" protein precipitates may be induced by a variety of ways. Examples include, but are not limited to: (a) affinity precipitation via complexation and specific interactions with appropriate cations, such as divalent cation salts (e.g., zinc, magnesium, calcium, cobalt, copper, iron, including salts thereof, both organic and inorganic); (b) salting out with Hofmeister series salts; (c) volume exclusion induced by addition of appropriate quantities of large polymers, such as polyethylene glycol (different molecular weights), dextran, etc.; and (d) isoelectric precipitation by a pH adjuster (acid or base).

The Hofmeister series salts originated from the ranking of various ions in their ability to precipitate a mixture of hen egg white proteins. Anions of these salts include, for example, thiocyanide, nitrate, fluoride, chloride, bromine, iodine, citrate, acetate, phosphate, and sulfate. Cations of these salts include, for example, calcium, magnesium, sodium, potassium, ammonium, tetramethyl ammonium, cesium and aluminum. The relative ability of the salts to precipitate a given protein depends on the nature of the protein, pH, and temperature, and can be experimentally determined.

Some embodiments of the present invention include at least one precipitating agent. Precipitating agents are known in the art. Examples of precipitating agents include, but are not limited to, divalent cations, such as zinc, copper, cobalt, iron, manganese, vanadium, cadmium, magnesium, calcium, and barium. Other precipitating agents include polyethylene glycol (PEG), dextran, polylysine, polyvinylpyrrolidone, and cyclodextrins. Still other precipitating agents include organic solvents like 2 methyl-2,4-pentane diol (MPD), dimethyl sulfoxide (DMSO), and ethanol. Divalent metal cations, particularly zinc, are used as the precipitating agents in one particular embodiment of the present invention.

Proteins probably form insoluble complexes with these cations through predominantly surface-exposed histidine residues and, to a lesser extent, cysteine, tryptophan, and glutamic acid residues. Zinc ions selectively precipitate proteins from solution by coordinating the lone pair electrons of heteroatoms on the side chains of these amino acids. Therefore, the present invention can be used to deliver proteins without limitation to the function, size, overall charge, or physical properties of the proteins. The majority of the precipitation at low protein concentrations is thought to occur due to the interprotein crosslinking between metal-ion and free surface groups. Precipitations using zinc are very rapid and are found to be kinetically irreversible. Protons in solution also compete with zinc ions for protein-binding sites; during the course of a metal precipitation there is usually a change in pH as protons are displaced from their coordination sites by the stronger binding zinc ions. This competitive binding offers possibilities for control of the kinetics of the dissolution process.

Divalent metal ions include, but are not limited to, the transition metal, and alkaline earth metal ions. Transitional metal ions such as zinc, copper, cobalt, and iron are particularly suitable. Zinc is the most preferred precipitating agent in the present invention. In some embodiments, monovalent metal ions, such as alkaline metals can be added.

While not wishing to be bound by theory, it appears that in some embodiments of the invention in which the divalent metal:glargine insulin is relatively high, the complexes of the present invention may be amorphous rather than crystalline. However, at ratios of 2 or 4:1 (divalent metal:glargine hexamer), the ratios are more likely to be crystalline. In some embodiments, amorphous complexes (higher ratios) may be mixed with crystalline complexes (lower ratios) to make compositions with a mixed release feature. Accordingly, the compositions of the present invention may contain at least about one of the following dry weight percentages of amorphous complexes: 0%, 1%, 2%, 4%, 6%, 8%, 10%, 15%, 20%, 30%, 40%, 50%, 60%, 70%, 80%, and 90%.

The compositions of the present invention typically comprise the precipitating agent at a solid weight percentage of about 0.1% to about 95%, more preferably about 10% to about 85%, yet more preferably about 30% to about 75%, and most preferably about 50% to about 70%. The composition may comprise no precipitating agent, because when the pharmaceutically useful protein is precipitated by salting out, volume exclusion or isoelectric precipitation, the precipitating agent only facilitates precipitation, rather than forming part of the insoluble complex. Once the precipitates form, the precipitating agent may optionally be removed from the suspension, leaving no or only trace amount of the precipitating agent in the final composition. The addition of excipient may also change the percentage of the precipitating agent. Thus, depending upon the amount of excipient, a composition of the present invention will comprise the precipitating agent at a solid weight percentage of less than about one of the following: 0.1%, 0.2%, 0.4%, 0.5%, 0.7%, 1.0%, 5%, 10%, 15%, or 20%.

In addition to the insulin derivative, the formulation may contain any protein useful as a therapeutic agent. The protein may also contain non-peptide moieties such as carbohydrate or lipid. Thus, these pharmaceutically useful proteins ("pharmaceutical proteins") of the present invention may include drugs which act on the peripheral nerves, adrenergic receptors, cholinergic receptors, the skeletal muscles, the cardiovascular system, smooth muscles, the blood circulatory system, synaptic sites, neuroeffector junctional sites, endocrine and hormone systems, the immunological system, the reproductive system, the skeletal system, autacoid systems, the alimentary and excretory systems, the histamine system, and the central nervous system. Suitable proteins may be selected from, for example, hypnotics and sedatives, psychic energizers, tranquilizers, respiratory drugs, anticonvulsants, muscle relaxants, antiparkinson agents (dopamine antagonists), analgesics, anti-inflammatories, antianxiety drugs (anxiolytics), appetite suppressants, antimigraine agents, muscle contractants, anti-infectives (antibiotics, antivirals, antifungals, vaccines) antiarthritics, antimalarials, antiemetics, anepileptics, bronchodilators, cytokines, growth factors, anti-cancer agents, antithrombotic agents, antihypertensives, cardiovascular drugs, antiarrhythmics, antioxidants, anti-asthma agents, hormonal agents including contraceptives, sympathomimetics, diuretics, lipid regulating agents, antiandrogenic agents, antiparasitics, anticoagulants, neoplastics, antineoplastics, hypoglycemics, nutritional agents and supplements, growth supplements, antienteritis agents, vaccines, antibodies, diagnostic agents, and contrasting agents. The pharmaceutical protein may act locally or systemically.

Examples of pharmaceutical proteins suitable for use in combination with the insulin derivative include but are not limited to calcitonin, erythropoietin (EPO), Factor VIII, Factor IX, ceredase, cerezyme, cyclosporin, granulocyte colony stimulating factor (GCSF), thrombopoietin (TPO), alpha-1 proteinase inhibitor, elcatonin, granulocyte macrophage colony stimulating factor (GMCSF), growth hormone, human growth hormone (HGH), growth hormone releasing hormone (GHRH), interferon alpha, interferon beta, interferon gamma, interleukin-1 receptor, interleukin-2, interleukin-1 receptor antagonist, interleukin-3, interleukin-4, interleukin-6, luteinizing hormone releasing hormone (LHRH), factor IX insulin, pro-insulin, insulin analogues (e.g., monoacylated insulin as described in U.S. Pat. No. 5,922,675), C-peptide, somatostatin, somatostatin analogs including octreotide, vasopressin, follicle stimulating hormone (FSH), insulin-like growth factor (IGF), insulintropin, macrophage colony stimulating factor (M-CSF), nerve growth factor (NGF), tissue growth factors, keratinocyte growth factor (KGF), glial growth factor (GGF), tumor necrosis factor (TNF), endothelial growth factors, parathyroid hormone (PTH), IIb/IIIa inhibitor, alpha-1 antitrypsin, phosphodiesterase (PDE) compounds, respiratory syncytial virus antibody, deoxyribonuclease (DNase), bactericidal/permeability increasing protein (BPI), anti-CMV antibody, and where applicable, analogues, agonists, antagonists, and inhibitors of the above, including the synthetic, native, glycosylated, unglycosylated, pegylated forms, and biologically active fragments and analogs thereof.

Compositions and corresponding doses of the pharmaceutical protein will vary with the bioactivity of the insulin derivative employed. The precise dosages can be determined by one skilled in the art when coupled with the pharmacodynamics and pharmacokinetics of the precise insulin derivative composition employed for a particular route of administration, and can readily be adjusted in response to periodic glucose monitoring.

Individual dosages (on a per inhalation basis) for inhaleable glargine insulin compositions are typically in the range of from about 2 mg to about 40 mg, about 4 mg to about 20 mg, or about 6 mg to about 10 mg insulin derivative, where the desired overall dosage is typically achieved in about 1-10 breaths, such as about 1 to 4 breaths. On average, the overall dose of glargine insulin administered by inhalation per day will range from about 0.1 U to about 20 U. The actual dose can be determined by a physician, based upon the need of the patient, whether insulin-naïve or existing insulin user, and based upon response to administration.

When the present invention is used to deliver glargine insulin by inhalation to the lung, the amount of glargine insulin in the composition will be that amount necessary to deliver a therapeutically effective amount of glargine insulin per unit dose to achieve at least one of the therapeutic effects of native insulin, i.e., the ability to control blood glucose levels to near normoglycemia. In practice, this will vary widely depending upon the severity of the diabetic condition to be treated, the patient population, the stability of the composition, and the like.

The composition will generally contain, in terms of solid weight, anywhere from about 1% to about 99%, such as from about 2% to about 95%, from about 5% to about 85%, or from about 70% to about 95%, of the pharmaceutical protein. The percentage of the pharmaceutical protein in the composition will also depend upon the relative amounts of excipients/additives contained in the composition. More specifically, the composition will typically contain at least about one of the following solid weight percentages of the pharmaceutical protein: 10%, 20%, 30%, 40%, 50%, 60%, 70%, 80%, 90% or more. In some embodiments, powder compositions will contain at least about 60%, e.g., about 60-100% by weight of the pharmaceutical protein. It is to be understood that more than one pharmaceutical protein may be incorporated into the compositions described herein. Furthermore, the composition may also contain more than one form of the pharmaceutical protein, for example glargine insulin and another type of insulin.

The molar ratio of the precipitating agent to the pharmaceutical protein in the compositions of the present invention may range from about 1:50 to about 50:1. The ratio is more generally from about 1:20 to about 20:1, or from about 1:10 to about 10:1, or from about 1:5 to about 5:1. The ideal molar ratio of the precipitating agent to the pharmaceutical protein may be determined by a person of ordinary skill in the art, and will generally be about one of the following: 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, 15:1, 20:1, 30:1, 40:1, 50:1, or greater.

One embodiment of the present invention provides compositions that contain no protamine. Protamines are a group of proteins isolated from fish, and are commonly used in insulin formulations to prolong duration (see, e.g., Vanbever R. et al., "Sustained release of insulin from insoluble inhaled particles," Drug Dev. Res. 48, 178-185, 1999). However, protamines, as well as protamine-insulin complexes, have been shown to be potentially immunogenic (Samuel T. et al., "Studies on the immunogenicity of protamines in humans and experimental animals by means of a micro-complement fixation test," Clin. Exp. Immunol. 33(2), 252-260 (1978); Kurtz A. B. et al., "Circulating IgG antibody to protamine in patients treated with protamine-insulins," Diabetologia. 25(4), 322-324 (1983)). Since the compositions of the present invention are capable of sustained release in the absence of protamine, the present invention provides the option of including no protamine, thereby avoiding the adverse reactions that may be caused by protamine.

While the use of liposomes is also commonly employed to sustain duration of drug effect, the present invention does not require the use of liposomes. Accordingly, other embodiments of the present invention provide compositions that contain no lipid, as well as compositions that contain no polymers, in addition to the pharmaceutical protein. However, having noted the possibility that the present compositions exclude lipids or the use of liposomes, it is also noted that the primary particles of the present invention can include lipids or be included into liposomal formulations, described in more detail below.

Excipients

As discussed herein, in some embodiments, an insulin derivative having a pI of about 6 to about 8 is administered in a formulation to the lungs, such that precipitation of the formulation occurs upon reaching the lung tissue. In this embodiment, the formulations are generally liquid or solid formulations.

Liquid formulations may be solutions of the insulin derivative, together with excipients, which promote the solubility of the insulin derivative prior to reaching the deep lung tissue. Upon reaching the deep lung tissue, where the pH is generally in the range of about 6 to 8, precipitation of the insulin derivative occurs.

Solid formulations may be powders of the insulin derivative, together with excipients, which promote the initial solubility of the insulin derivative upon reaching the deep lung tissue. After some period of solubility, however, the physiological pH of the lung tissue causes the precipitation of the insulin derivative.

In both the solid and liquid formulations discussed herein, the excipients are carefully chosen to ensure that precipitation occurs and is maintained in the lung. Thus, excipient choices are made to minimize interference with the precipitation reaction. Thus, for example, an excipient that chelates a precipitating agent, such as a metal cation in the formulation, may be undesirable. Similarly, excipients that increase osmotic pressure around the insulin derivative upon reaching the deep lung tissue may also be undesirable; such excipients can unduly increase local water volume, thereby slowing the rate of precipitation. Still further, the amount of excipient in the formulation should also be carefully chosen to minimize any interfering effect.

The following groups of excipients may be used in some embodiments of the formulations of the present invention.

Buffering Agents

Noting that glargine insulin has an isoelectric point of 6.7, and that some degree of initial solubility of the formulation may be desirable upon reaching the distal lung, the compositions of the invention may further include one or more buffering, or pH-adjusting or -controlling, agents. These agents are generally a salt prepared from an organic acid or base. Representative buffers include organic acid salts of citric acid, ascorbic acid, gluconic acid, carbonic acid, tartaric acid, succinic acid, acetic acid, or phthalic acid, Tris, tromethamine hydrochloride, or phosphate buffers. Suitable amino acids, which may also function in a buffering capacity, include alanine, glycine, arginine, betaine, histidine, glutamic acid, aspartic acid, cysteine, lysine, leucine, isoleucine, valine, methionine, phenylalanine, aspartame, tyrosine, tryptophan, and the like.

These agents, if present, are generally present in amounts of from about 0.01% to about 10%, by weight, of the composition. In some embodiments, the amount ranges from about 0.02% to about 9%, or from about 0.03% to about 8%, or from about 0.04% to about 7%, or from about 0.05% to about 6%, by weight, of the composition. The amount chosen will depend upon its desired effect on the composition and can be varied as needed.

Dry Formulation-Enhancing Excipients

Some embodiments of the invention are dry formulations designed for pulmonary delivery. Some embodiments of the invention include excipients that are designed to impart desired physical characteristics to the end product, which may further impart desired or improved actions on the treated subject. Thus, the inventive compositions may comprise a pharmaceutically acceptable excipient or carrier, which may be taken into the lungs with no significant adverse toxicological effects to the subject, and particularly to the lungs of the subject.

Generally, such excipients will, if present, at least in part, serve to further improve the features of the active agent composition, for example by providing more efficient and/or reproducible delivery of the active agent, improve the handling characteristics of powders, such as flowability and consistency, and/or facilitate manufacturing and/or filling of unit dosage forms. In particular, excipient materials can often function to further improve the physical and chemical stability of the active agent, minimize the residual moisture content and hinder moisture uptake, and to enhance particle size, degree of aggregation, particle surface properties, such as rugosity, ease of inhalation, and the targeting of particles to the lung. One or more excipients may also be provided to serve as bulking agents when it is desired to reduce the concentration of active agent in the formulation. It is also noted that because of the desire to achieve precipitation in the distal lung, which process may be slowed by the presence of excess fluid, excipients may be chosen to minimize their osmotic effect on the formulation.

One particular type of dry formulation-enhancing excipient that may be included in the formulation is the dispersibility-enhancing excipient. This excipient generally provides more efficient and/or reproducible delivery of the glargine insulin, by improving the physical characteristics of the dry formulation. Dispersibility-enhancing agents include, but are not limited to, amino acids and polypeptides that function as dispersing agents. Amino acids falling into this category include, but are not limited to, hydrophobic amino acids such as leucine, norleucine, valine, isoleucine, tryptophan, alanine, methionine, phenylalanine, tyrosine, histidine, and proline. Dispersibility-enhancing peptide excipients include dimers, trimers, tetramers, and pentamers comprising one or more hydrophobic amino acid components such as those described above. Examples include, but are not limited to, dileucine and trileucine.

These excipients, if present, are generally present in the composition in amounts ranging from about 0.01% to about 95%, such as about 0.5% to about 80%, or about 1% to about 60%, by weight. The amount can be from about 10% to about 60%, or from about 20% to about 50%, or from about 30% to about 40%, or about 35%, by weight of the composition. The amount chosen will depend upon its desired effect on the composition and can be varied as needed. The ideal amount and type of dry formulation-enhancing excipient is an amount and type that furthers dispersability and deliverability of the glargine insulin, but which does not significantly hinder the precipitation equilibrium.

Glass Transition Stabilizing Excipients

Some embodiments of the invention are dry formulations, and some may benefit from the addition of a component that stabilizes the glass transition temperature of the composition. In some embodiments, this component will have a higher glass transition temperature than the glargine insulin. In some embodiments, the excipient may have a glass transition temperature (Tg) above about 35° C., such as above about 40° C., above about 45° C., above about 55° C., above about 60° C., above about 65° C., above about 70° C., above about 75° C., above about 80° C., above about 85° C., or above about 90° C., as measured by differential scanning calorimetry (DSC).

Glass transition stabilizing excipients, also known as glass stabilizers, glass transition stabilizers, and glass formers, include, but are not limited to, carbohydrates. Carbohydrate excipients suitable for use in the invention include, for example, monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), pyranosyl sorbitol, myoinositol, and the like. Other examples of glass formers are described in U.S. Pat. No. 6,309,671, the entire disclosure of which is incorporated by reference herein.

The glass transition stabilizing excipients, if present, will generally be present in an amount by weight of from about 1% to about 50% of the composition. In some embodiments, they are present in an amount from about 2% to about 25%, or from about 4% to about 12%, or from about 5% to about 10%, or about 7%, by weight of the composition. The amount may be 10, 20, 30, 40, or 50%, by weight, of the composition. The amount chosen will depend upon its desired effect on the composition and can be varied as needed. The ideal amount and type of glass transition stabilizing excipient is an amount and type that furthers dispersability and deliverability of the glargine insulin, but which does not significantly hinder the precipitation equilibrium.

Other pharmaceutical excipients and additives useful in the present pharmaceutical formulation include, but are not limited to, amino acids, peptides, proteins, non-biological polymers, biological polymers, carbohydrates, such as sugars, derivatized sugars such as alditols, aldonic acids, esterified sugars, and sugar polymers, which may be present singly or in combination. Exemplary protein excipients include albumins such as human serum albumin (HSA), recombinant human albumin (rHA), gelatin, casein, hemoglobin, and the like. Suitable excipients are those provided in U.S. Pat. No. 6,136,346 and WO 96/32096, which are incorporated herein by reference in their entireties.

The inventive compositions may also include polymeric excipients/additives, e.g., polyvinylpyrrolidones, derivatized celluloses such as hydroxymethylcellulose, hydroxyethylcellulose, and hydroxypropylmethylcellulose, Ficolls (a polymeric sugar), hydroxyethylstarch, dextrates (e.g., cyclodextrins, such as 2-hydroxypropyl-β-cyclodextrin and sulfobutylether-β-cyclodextrin), polyethylene glycols, and pectin. In one or more embodiments, the formulation is polymer free.

The inventive compositions may further include flavoring agents, taste-masking agents, inorganic salts (for example sodium chloride), antimicrobial agents (for example benzalkonium chloride), sweeteners, antioxidants, antistatic agents, surfactants (for example polysorbates such as "TWEEN 20" and "TWEEN 80"), sorbitan esters, lipids (for example phospholipids such as lecithin and other phosphatidylcholines, phosphatidylethanolamines), fatty acids and fatty esters, steroids (for example cholesterol), and chelating agents (for example EDTA, zinc and other such suitable cations). Other pharmaceutical excipients and/or additives suitable for use in the compositions according to the invention are listed in "Remington: The Science & Practice of Pharmacy", $21^{st}$ ed., Lippincott, Williams & Wilkins, (2005), and in the "Physician's Desk Reference", $60^{th}$ ed., Medical Economics, Montvale, N.J. (2006), both of which are incorporated herein by reference in their entireties.

For metered-dose inhaler (MDI) applications, the compositions may also be treated so as to have even greater stability. Several attempts have dealt with improving suspension stability by increasing the solubility of surface-active agents in the HFA (hydrofluoroalkane) propellants. To this end, U.S. Pat. No. 5,118,494, and WO 91/11173 and WO 92/00107 disclose the use of HFA soluble fluorinated surfactants to improve suspension stability. Mixtures of HFA propellants with other perfluorinated cosolvents have also been disclosed as in WO 91/04011. Other attempts at stabilization involve the inclusion of nonfluorinated surfactants. In this respect, U.S. Pat. No. 5,492,688 discloses that some hydrophilic surfactants (with a hydrophilic/lipophilic balance greater than or equal to 9.6) have sufficient solubility in HFAs to stabilize medicament suspensions. Increases in the solubility of conventional nonfluorinated MDI surfactants (e.g. oleic acid, lecithin) can also reportedly be achieved with the use of co-solvents such as alcohols, as set forth in U.S. Pat. Nos. 5,683,677 and 5,605,674, as well as in WO 95/17195. All of the aforementioned references are incorporated herein by reference in their entireties.

Some embodiments of the compositions in accordance with the present invention may exclude penetration enhancers, which can cause irritation and are toxic at the high levels often necessary to provide substantial enhancement of absorption. Specific enhancers, which are typically absent from the compositions of the present invention, are the detergent-like enhancers such as deoxycholate, laureth-9, DDPC, glycocholate, and the fusidates. Certain enhancers, however, such as those that protect the pharmaceutical protein from enzyme degradation, e.g., protease and peptidase inhibitors such as alpha-1 antiprotease, captropril, thiorphan, and the HIV protease inhibitors, may, in certain embodiments of the present invention, be incorporated in the composition of the present invention.

Generally, the pharmaceutical formulations of the present invention will contain from about 1% to about 90% by weight excipient, or from about 5%-80% by weight excipient, or from about 15-60% by weight excipient. In some embodiments, spray-dried formulations will contain from about 0-50% by weight excipient, or from 0-40% by weight excipient. In general, a high concentration of the pharmaceutical protein is desired in the final pharmaceutical formulation.

While much of the present discussion has related to excipients that can be included in the invention, the present invention also expressly contemplates the exclusion of certain elements. Generally, the description of any group or list of compounds, elements, components, etc., is to be taken as an express contemplation of the exclusion of any member of such group or list. In particular, the exclusion of polymers from the present invention is expressly contemplated.

Formulations

The compositions described herein may be in powdered form (e.g., including particles of the invention) or may be flowable liquids. Liquid formulations are preferably solutions in which the active drug is dissolved in a solvent (e.g., water, ethanol, ethanol-water, saline) and less preferably are colloidal suspensions. The liquid formulation may also be a solution or suspension of the glargine insulin in a low boiling point propellant.

Liquid formulations containing dileucyl-containing peptides, including, but not limited to dileucine and trileucine, are also highly dispersible, possessing high ED values.

Some embodiments of the invention include particles that have physical characteristics that allow for their delivery to the deep lung. In one embodiment, a powdered or liquid formulation for use in the present invention includes an aerosol having a particle size selected to permit penetration into the alveoli of the lungs. Dry powders of the present invention are composed of aerosolizable particles effective to penetrate into the lungs. The particles of the present invention may generally have a mass median diameter (MMD), or volume median geometric diameter (VMGD), or mass median envelope diameter (MMED), or a mass median geometric diameter (MMGD), of less than about 30 µm, or less than about 20 µm, or less than about 10 µm, or less than about 7.5 µm, or less than about 4 µm, or less than about 3.3 µm, and usually are in the range of 0.1 µm to 5 µm in diameter. Preferred powders are composed of particles having an MMD, VMGD, MMED, or MMGD from about 1 to 5 µm. In some cases, the powder will also contain non-respirable carrier particles such as lactose, where the non-respirable particles are typically greater than about 40 microns in size. Generally particles having an MMD of 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30 µm are contemplated, as are values less than any of these discrete values, as well as ranges from any of these discrete values to any of these discrete values, such as from 1-30 µm, or from 7-16 µm, or from 11-29 µm, etc.

The powders of the present invention may also be characterized by an aerosol particle size distribution—mass median aerodynamic diameter (MMAD)—having MMADs less than about 10, 9, 8, 7, 6, or 5 µm, or less than 4.0 µm, even more preferably less than 3.3 µm, and most preferably less than 3 µm. The mass median aerodynamic diameters of the powders will characteristically range from about 0.1-5.0 µm, or from about 0.2-5.0 µm MMAD, or from about 1.0-4.0 µm MMAD, or from about 1.5 to 3.0 µm. Small aerodynamic diameters may be achieved by a combination of optimized spray drying conditions and choice and concentration of excipients. Generally particles having an MMAD of 1, 2, 3, 4, 5, 6, 7, 8, 9, 10, 11, 12, 13, 14, 15, 16, 17, 18, 19, and 20 are contemplated, as are values less than any of these discrete values, and ranges from any of these discrete values to any of these discrete values, such as from 1-20 µm, or from 7-16 µm, or from 11-19 µm, etc.

The powders of the present invention may also be characterized by their densities. The powder will generally possess a bulk density from about 0.1 to 10 g/cubic centimeter, or from about 0.1-2 g/cubic centimeter, or from about 0.15-1.5 g/cubic centimeter. In one embodiment of the present invention, the powders have big and fluffy particles with a density of less than about 0.4 g/cubic centimeter and an MMD between 5 and 30 microns. It is worth noting that the relationship of diameter, density and aerodynamic diameter can be determined by the following formula (Gonda, "Physicochemical principles in aerosol delivery," in Topics in Pharmaceutical Sciences 1991, Crommelin, D. J. and K. K. Midha, Eds., Medpharm Scientific Publishers, Stuttgart, pp. 95-117, 1992.).

When in a dry powder form, the pharmaceutical formulation may have a moisture content below about 10 wt %, such as below about 5 wt %, or below about 3 wt %. Such powders are described in WO 95/24183, WO 96/32149, WO 99/16419, and WO 99/16422, all of which are incorporated herein by reference in their entireties.

Some particles according to the invention are formed in such a manner that the compositions are uniformly distributed throughout the particle. That is, the glargine insulin, as well as other elements of the composition, which may include precipitating agent, buffer, dispersibility-enhancing agent, and/or glass-stabilizing agent, are uniformly distributed throughout the particle.

In other embodiments of the invention, particles are formed in such a way as to enrich particular elements of the formulation in particular sections of the particle. For example, a particle may generally be described as including a core at its center and a surface around its periphery. With regard to the heterogeneity within the particle, the transition from core to surface may be gradual or abrupt, or any variation thereof.

Particles may be manufactured such that a core is enriched with one element and a surface is enriched with another.

This heterogeneity may be achieved by forming the core and surface in separate preparation steps, using different compositional elements during the different steps. Alternatively, the heterogeneity may be achieved by introducing into a homogeneous mixture a component that has an affinity for a particular section of a particle or which migrates during a drying phase, for example. Examples of such methods are described in U.S. Pat. No. 6,518,239, the entire disclosure of which is incorporated herein by reference.

In one embodiment of the invention, heterogeneous particles are formed by forming a liquid composition comprising glargine insulin and one or more excipients. The liquid composition may additionally include at least one surface excipient, which is an agent that has a tendency to migrate to the surface of the particle. Such surface excipients may be "surface active agents," as described in U.S. Pat. No. 6,518,239. Examples of such agents include, but are not limited to, di- and tripeptides containing at least two leucines.

A particular characteristic that usually relates to improved dispersibility and handling characteristics is the product rugosity. Rugosity is the ratio of the specific area (e.g., as measured by BET, molecular surface adsorption, or other conventional technique) and the surface area calculated from the particle size distribution (e.g., as measured by centrifugal sedimentary particle size analyzer, Horiba Capa 700) and particle density (e.g., as measured by pycnometry), assuming non-porous spherical particles. Rugosity may also be measured by air permeametry. If the particles are known to be generally nodular in shape, as is the case in spray drying, rugosity is a measure of the degree of convolution or folding of the surface. This may be verified for powders made by the present invention by SEM analysis. A rugosity of 1 indicates that the particle surface is spherical and non-porous. Rugosity values greater than 1 indicate that the particle surface is non-uniform and convoluted to at least some extent, with higher numbers indicating a higher degree of non-uniformity. For the powders of the present invention, it has been found that particles may have a rugosity of at least about 2, such as at least about 3, at least about 4, or at least about 5, and may range from 2 to 10, such as from 4 to 8, or from 4 to 6.

The drying operation may be controlled to provide dried particles having particular characteristics, such as a rugosity above 2, as discussed above. Rugosities above 2 may be obtained by controlling the drying rate so that a viscous layer of material is rapidly formed on the exterior of the droplet. Thereafter, the drying rate should be sufficiently rapid so that the moisture is removed through the exterior layer of material, resulting in collapse and convolution of the outer layer to provide a highly irregular outer surface. The drying should not be so rapid, however, that the outer layer of material is ruptured. The drying rate may be controlled based on a number of variables, including the droplet size distribution, the inlet temperature of the gas stream, the outlet temperature of the gas stream, the inlet temperature of the liquid droplets, and the manner in which the atomized spray and hot drying gas are mixed.

Powder surface area, measured by nitrogen adsorption, typically range from about 6 m2/g to about 13 m2/g, such as from about 7 m2/g to about 10 m2/g. The particles often have a convoluted "raisin" structure rather than a smooth spherical surface.

Preparing Compositions

The compositions of one or more embodiments of the present invention may be made by any of the various methods and techniques known and available to those skilled in the art.

Dry powder formulations may be prepared, for example, by spray drying (or freeze drying or spray-freeze drying). Spray drying of the formulations is carried out, for example, as described generally in the "Spray Drying Handbook", $5^{th}$ ed., K. Masters, John Wiley & Sons, Inc., NY, N.Y. (1991), and in WO 97/41833, the contents of which are incorporated herein by reference.

The glargine insulin compositions of the invention can be spray-dried from an aqueous solution. Utilizing this approach, the glargine insulin is first dissolved in water, generally containing a physiologically acceptable buffer or other excipient as describe above. The pH range of active agent-containing solutions is generally between about 4 and 6. The aqueous formulation may optionally contain additional water-miscible solvents, such as acetone, alcohols, and the like. Representative alcohols are lower alcohols such as methanol, ethanol, propanol, isopropanol, and the like. The pre-spray dried solutions will generally contain solids dissolved at a concentration from 0.01% (weight/volume) to about 20% (weight/volume), usually from 0.1% to 3% (weight/volume). Dispersibility-enhancing agent, glass-stabilizing agent, and/or precipitating agent may be included in the solution.

The solutions are then spray dried in a spray drier, such as those available from commercial suppliers such as Niro A/S (Denmark), Buchi (Switzerland) and the like, resulting in a dispersible, dry powder. Optimal conditions for spray drying the solutions will vary depending upon the formulation components, and are generally determined experimentally. The gas used to spray dry the material is typically air, although inert gases such as nitrogen or argon are also suitable. Moreover, the temperature of both the inlet and outlet of the gas used to dry the sprayed material is such that it does not cause decomposition of the active agent in the sprayed material. Such temperatures are typically determined experimentally, although generally, the inlet temperature will range from about 50° C. to about 200° C. while the outlet temperature will range from about 30° C. to about 150° C.

Variations of the above may be utilized. One such process is described in U.S. Pat. No. 5,985,248, assigned to Nektar Therapeutics, which document is incorporated herein by reference in its entirety. In this method, a hydrophobic drug is dissolved in an organic solvent or co-solvent system, and the hydrophilic components (e.g., the leucyl-containing peptides and optional other excipients) are at least partially dissolved in the same organic solvent or co-solvent system. The resulting solution is then spray-dried to form particles. Typically, the solubility of the active agent and the hydrophilic component will govern the selection of the organic solvent system. The organic solvent is selected to provide a solubility for the hydrophilic component of at least 1 mg/ml, and preferably at least 5 mg/ml, and a solubility for the hydrophobic drug of at least 0.01 mg/ml, preferably at least 0.05 mg/ml.

Alternatively, the composition may be prepared by spray-drying a suspension, as described in U.S. Pat. No. 5,976,574, assigned to Nektar Therapeutics, which document is incorporated herein by reference in its entirety. In this method, the hydrophobic drug is dissolved in an organic solvent, e.g., methanol, ethanol, isopropanol, acetone, heptane, hexane chloroform, ether, followed by suspension of the hydrophilic excipient in the organic solvent to form a suspension. The suspension is then spray-dried to form particles. Preferred solvents, for both of the above spray-drying methods include alcohols, ethers, ketones, hydrocarbons, polar aprotic solvents, and mixtures thereof.

The dry powders of the invention may also be prepared by combining aqueous solutions or suspensions of the formulation components and spray-drying them simultaneously in a spray-dryer, as described in U.S. Pat. No. 6,001,336, assigned to Nektar Therapeutics, which document is incorporated herein by reference in its entirety. Alternatively, the dry powders may be prepared by preparing an aqueous solution of a hydrophilic excipient or additive, preparing an organic solution of a hydrophobic drug, and spray drying the aqueous solution and the organic solution simultaneously through a nozzle, e.g., a coaxial nozzle, to form a dry powder, as described in WO 98/29096, which is incorporated herein by reference in its entirety.

Alternatively, powders may be prepared by lyophilization, vacuum drying, spray-freeze drying, super critical fluid processing, air drying, or other forms of evaporative drying. In some instances, it may be desirable to provide the dry powder formulation in a form that possesses improved handling/processing characteristics, e.g., reduced static, better flowability, low caking, and the like, by preparing compositions composed of fine particle aggregates, that is, aggregates or agglomerates of the above-described dry powder particles, where the aggregates are readily broken back down to the fine powder components for pulmonary delivery, as described, e.g., in U.S. Pat. No. 5,654,007, which is incorporated herein by reference in its entirety.

In another approach, dry powders may be prepared by agglomerating the powder components, sieving the materials to obtain agglomerates, spheronizing to provide a more spherical agglomerate, and sizing to obtain a uniformly-sized product, as described, e.g., in WO 95/09616, which is incorporated herein by reference in its entirety.

Dry powders may also be prepared by blending, grinding, sieving or jet milling formulation components in dry powder form.

Once formed, the dry powder compositions are preferably maintained under dry (i.e., relatively low humidity) conditions during manufacture, processing, and storage. Irrespective of the drying process employed, the process will preferably result in respirable, highly dispersible particles comprising the glargine insulin, a precipitating agent, and any other desired excipients.

Packaging and Containers

Unit dose pharmaceutical compositions may be contained in a container. Examples of containers include, but are not limited to, capsules, blisters, vials, ampoules, or container closure systems made of metal, polymer (e.g., plastic, elastomer), glass, or the like.

The container may be inserted into an aerosolization device. The container may be of a suitable shape, size, and material to contain the pharmaceutical composition and to provide the pharmaceutical composition in a usable condition. For example, the capsule or blister may comprise a wall, which comprises a material that does not adversely react with the pharmaceutical composition. In addition, the wall may comprise a material that allows the capsule to be opened to allow the pharmaceutical composition to be aerosolized. In one version, the wall comprises one or more of gelatin, hydroxypropyl methylcellulose (HPMC), polyethyleneglycol-compounded HPMC, hydroxyproplycellulose, agar, aluminum foil, or the like. In one version, the capsule may comprise telescopically adjoining sections, as described for example in U.S. Pat. No. 4,247,066, which is incorporated herein by reference in its entirety. The size of the capsule may be selected to adequately contain the dose of the pharmaceutical composition. The sizes generally range from size 5 to size 000 with the outer diameters ranging from about 4.91 mm to 9.97 mm, the heights ranging from about 11.10 mm to about 26.14 mm, and the volumes ranging from about 0.13 mL to about 1.37 mL, respectively. Suitable capsules are available commercially from, for example, Shionogi Qualicaps Co. in Nara, Japan and Capsugel in Greenwood, S.C. After filling, a top portion may be placed over the bottom portion to form a capsule shape and to contain the powder within the capsule, as described in U.S. Pat. Nos. 4,846,876 and 6,357,490, and in WO 00/07572, which are incorporated herein by reference in their entireties. After the top portion is placed over the bottom portion, the capsule can optionally be banded.

Administration of the Compositions

The compositions of one or more embodiments of the present invention may be administered by any of the various methods and techniques known and available to those skilled in the art.

For example, in one or more embodiments, the compositions described herein may be delivered using any suitable dry powder inhaler (DPI), i.e., an inhaler device that utilizes the patient's inhaled breath as a vehicle to transport the dry powder drug to the lungs. Preferred are Nektar Therapeutics' dry powder inhalation devices as described in U.S. Pat. Nos. 5,458,135; 5,740,794; and 5,785,049, the disclosures of which are incorporated herein by reference in their entireties.

When administered using a device of this type, the powder is contained in a receptacle having a puncturable lid or other access surface, preferably a blister package or cartridge, where the receptacle may contain a single dosage unit or multiple dosage units. Convenient methods for filling large numbers of cavities (i.e., unit dose packages) with metered doses of dry powder medicament are described, e.g., in WO 97/41031 (1997), which is incorporated herein by reference in its entirety.

Also suitable for delivering the powders described herein are dry powder inhalers of the type described, for example, in U.S. Pat. Nos. 3,906,950 and 4,013,075, which are incorporated herein by reference in their entireties, wherein a premeasured dose of dry powder for delivery to a subject is contained within a hard gelatin capsule.

Other dry powder dispersion devices for pulmonarily administering dry powders include those described, for example, in EP 129985; EP 472598; EP 467172; and U.S. Pat. No. 5,522,385, which are incorporated herein by reference in their entireties. Also suitable for delivering the dry powders of the invention are inhalation devices such as the Astra-Draco "TURBUHALER". This type of device is described in detail in U.S. Pat. Nos. 4,668,281; 4,667,668; and 4,805,811, all of which are incorporated herein by reference in their entireties. Other suitable devices include dry powder inhalers such as the ROTAHALER™ (Glaxo), Discus™ (Glaxo), Spiros™ inhaler (Dura Pharmaceuticals), and the Spinhaler™ (Fisons). Also suitable are devices which employ the use of a piston to provide air for either entraining powdered medicament, lifting medicament from a carrier screen by passing air through the screen, or mixing air with powder medicament in a mixing chamber with subsequent introduction of the powder to the patient through the mouthpiece of the device, such as described in U.S. Pat. No. 5,388,572, which is incorporated herein by reference in its entirety.

Dry powders may also be delivered using a pressurized, metered dose inhaler (MDI), e.g., the Ventolin™ metered dose inhaler, containing a solution or suspension of drug in a pharmaceutically inert liquid propellant, e.g., a chlorofluorocarbon or fluorocarbon, as described in U.S. Pat. Nos. 5,320,094 and 5,672,581, which are both incorporated herein by reference in their entireties.

Prior to use, dry powders are generally stored under ambient conditions, and preferably are stored at temperatures at or below about 25° C., and relative humidities (RH) ranging from about 30 to 60%. More preferred relative humidity conditions, e.g., less than about 30%, may be achieved by the incorporation of a desiccating agent in the secondary packaging of the dosage form.

The time for dosing is typically short. For a single capsule or blister (e.g., 5 mg dose), the total dosing time is normally less than about 1 minute. A 2 capsule or blister dose (e.g., 10 mg) usually takes about 1 minute. A 5 capsule or blister dose (e.g., 25 mg) may take about 3.5 minutes to administer. Thus, the time for dosing may be less than about 5 minutes, such as less than about 4 minutes, less than about 3 minutes, less than about 2 minutes, or less than about 1 minute.

Alternatively, the compositions described herein may be administered by nebulization. For example, a dry powder may be dissolved or suspended in a solvent, e.g., water, ethanol, or saline. Nebulizers for delivering an aerosolized solution include the AERx™ (Aradigm), the Ultravent™ (Mallinkrodt), and the Acorn II™ (Marquest Medical Products).

Liquid formulations can be atomized by any of a variety of procedures. For example, the liquid can be sprayed through a two-fluid nozzle, a pressure nozzle, or a spinning disc, or atomized with an ultrasonic nebulizer or a vibrating orifice aerosol generator (VOAG). In one or more embodiments, a liquid formulation is atomized with a pressure nozzle, such as a BD AccuSpray nozzle. Thus, aerosolization apparatuses may be based on condensation aerosolization, an impinging jet technique, electrospray techniques, thermal vaporizing, or a Peltier device.

Jet nebulizers involve use of air pressure to break a liquid solution into aerosol droplets. In one or more embodiments, a jet nebulizer (e.g., Aerojet, AeroEclipse, Pari L. C., the Parijet, Whisper Jet, Microneb®, Sidestream®, Acorn II®, Cirrus and Upmist®) generates droplets as a mist by shattering a liquid stream with fast moving air supplied by tubing from an air pump. Droplets that are produced by this method typically have a diameter of about 2-5 µm.

In one or more embodiments, an ultrasonic nebulizer that uses a piezoelectric transducer to transform electrical current into mechanical oscillations is used to produce aerosol droplets. Examples of ultrasonic nebulizers include, but are not limited to, the Siemens 345 UltraSonic Nebulizer™ and ones commercially available from, for example, Omron Heathcare, Inc. and DeVilbiss Health Care, Inc. See, e.g., EP 1 066 850, which is incorporated by reference herein in its entirety. The resulting droplets typically have an MMAD in the range of about 1 to about 5 microns.

Vibrating porous plate nebulizers work by using a sonic vacuum produced by a rapidly vibrating porous plate to extrude a solvent droplet through a porous plate. See, e.g., U.S. Pat. Nos. 5,758,637; 5,938,117; 6,014,970; 6,085,740; and 6,205,999, which are incorporated herein by reference in their entireties.

For example, in one or more embodiments, the aerosol generator is the commercially available Aerogen (available from Nektar Therapeutics, San Carlos, Calif.) aerosol generator which comprises a vibrational element and dome-shaped aperture plate with tapered holes. When the plate vibrates several thousand times per second, such as about 100 k/s to about 150 k/s, a micro-pumping action causes liquid to be drawn through the tapered holes, creating a low-velocity aerosol with a precisely defined range of droplet sizes. The Aerogen aerosol generator does not require propellant.

In the Aerogen Aeroneb and Pari eFlow (Pari Respiratory Equipment, Germany), a piezoelectric oscillator is placed circumferentially around the vibrating mesh and vibrations shake precisely sized droplets of the nebulizer content through the membrane, to form a respirable mist of medication on the other side. In another vibrating mesh nebulizer, the Omron Micro-air (Omron, Japan), the piezoelectric oscillator is positioned proximal to the vibrating mesh instead of circumferentially around it, pushing rather than shaking droplets of droplets of nebulizer content through the pores in the membrane with a similar result.

In condensation aerosol generators, the aerosol is formed by pumping drug formulation through a small, electrically heated capillary. Upon exiting the capillary, the formulation is rapidly cooled by ambient air, and a gentle aerosol is produced that is relatively invariant to ambient conditions and the user inhalation rate. See, e.g., U.S. Pat. No. 6,701,922 and WO 03/059413, which are incorporated herein by reference in their entireties. In one or more embodiments, the condensation aerosol generator comprises one disclosed by Alexza Molecular Delivery Corporation. See, e.g., U.S. Published Application No. 2004/0096402, which is incorporated herein by reference in its entirety.

Another apparatus for delivery of a metered quantity of a liquid pharmaceutical composition for inhalation is described for example in WO 91/14468 and WO 97/12687, which are incorporated herein by reference in their entireties. The nebulizers described therein are known by the name Respimat®.

One or more electrosprays may be used to nebulize liquid formulations. The term electrostatic spray (also known as electrohydrodynamic spray or electrospray) refers to systems in which the dispersion of the liquid relies on its electric charging, so that nebulization and gas flow processes are relatively uncoupled. Examples of electrospray devices are disclosed in U.S. Pat. Nos. 6,302,331; 6,583,408; and 6,803,565, which are incorporated herein by reference in their entireties.

In one or more embodiments, the aerosol generator comprises a thermal vaporizing device. Such a device may be based on inkjet technology.

In one or more embodiments, the aerosol generator comprises a Peltier device. An example of such a device is disclosed in U.S. Published Application No. 2004/0262513, which is incorporated herein by reference in its entirety.

In one or more embodiments, the aerosol generator comprises a vibrating orifice monodisperse aerosol generator (VOAG). This device is an example of one type of monodisperse aerosol generator.

In one or more embodiments, the aerosol generator comprises a thin film, high surface area boiler that relies on capillary force and phase transition. By inducing phase transition in a capillary environment, pressure is imparted onto the expanding gas, which is ejected. This technology has been disclosed by Vapore, Inc., and is known as Vapore-Jet CFV technology. See, e.g., U.S. Pat. Nos. 5,692,095; 5,870,525; 6,162,046; 6,347,936; 6,585,509; and 6,634,864, and U.S. application Ser. No. 10/691,067, which are all incorporated herein by reference in their entireties.

Active agents may be delivered simultaneously, some preferred order, and/or providing one agent in an aerosol of a certain size to target one region of the lung while providing another in another size to target another region. Thus, purposeful variation of the aerosol size can cause some aerosol to deposit more proximally near the endotracheal tube to treat that area, while also sending in small aerosol to penetrate more deeply.

Utility

The compositions of the invention are useful, when administered pulmonarily in a therapeutically effective amount to a mammalian subject, for treating or preventing any condition responsive to the administration of the pharmacologically active compound in the formulation. For example, in cases in which the pharmacologically active compound is glargine insulin, the condition being treated may be diabetes. Thus, for example, the present invention finds use in the treatment of diabetes.

The following examples are illustrative of the present invention, and are not to be construed as limiting the scope of the invention. Variations and equivalents of this example will be apparent to those of skill in the art in light of the present disclosure, the drawings, and the claims herein. Unless otherwise stated, all percentages are by weight of the total composition.

EXAMPLES

Example 1

Dose Range Finding of Insulin Glargine Following Administration Via Intratracheal Instillation to Sprague-Dawley Rats This Example evaluates the dose of insulin glargine required to achieve a target blood glucose reduction when administered to rats via intratracheal instillation.

Materials and Methods

LANTUS® insulin glargine (Aventis Pharmaceuticals, Inc., Kansas City, Mo. [lot #40D 058]) is a recombinant human insulin analog which provides a longer duration of activity (up to 24 hours in humans) than that of regular insulin; it differs from human insulin in that the amino acid asparagine at position A21 is replaced by glycine, and two arginines are added to the C-terminus of the B-chain (molecular weight of 6063 Dalton). Insulin glargine was reformulated for intratracheal administration.

Briefly, five doses ranging from 80-960 µg/animal were compared in parallel where Groups 1-5 received the selected doses of the glargine insulin formulation on the same day. The doses were evaluated to achieve nadir blood glucose concentrations between approximately 40 and 60 mg/dL after compound administration.

The test system included 10 pre-cannulated (jugular vein catheter [JVC]) adult male fasted (~17 hours) Sprague-Dawley rats (Hilltop Lab Animals, Inc., Scottdale, Pa.). Ten animals weighing between 0.313-0.367 kg were used. Prior to dosing, the rats were lightly anesthetized by inhaled Isoflurane (Abbott Laboratories, Chicago, Ill.). Each animal was administered the target dose of the glargine insulin formulation by IT instillation into the lungs. Venous blood samples of approximately 0.4 mL were collected from the JVC at the following time points: predose (~1 hour prior to dosing), 20, 60, 120, 180, 240, 480, and 720 minutes post-dose. Two readings of whole blood glucose concentration (mg/dL) per time point were made using the Glucometer Elite glucose monitor (Bayer Corp., Elkart, Ind.). The remaining portion of the blood sample was processed into plasma and stored at −80° C. for later testing (data not shown). Pharmacodynamic analysis was performed using Microsoft Office Excel 2003.

Table 1 shows the study design.

TABLE 1

| Group No. | Control/Test Article | Route of Administration | No. of Animals/Gender | Total Dose of Insulin (µg/animal) | Dose Volume (µL) | No. of Days of Dosing |
|---|---|---|---|---|---|---|
| 1 | LANTUS ® insulin glargine | IT | 2/M | 80 | 300 | 1 |
| 2 | LANTUS ® insulin glargine | IT | 2/M | 160 | 300 | 1 |
| 3 | LANTUS ® insulin glargine | IT | 2/M | 320 | 300 | 1 |
| 4 | LANTUS ® insulin glargine | IT | 2/M | 640 | 300 | 1 |
| 5 | LANTUS ® insulin glargine | IT | 2/M | 960 | 300 | 1 |

Results

Table 2 shows individual and mean body weights. Table 3 shows individual and mean blood glucose concentrations.

TABLE 2

| Group | Animal | Gender | Date of Birth | Body Weight (kg) |
|---|---|---|---|---|
| 1 | 1 | Male | 12 OCT. 2004 | 0.313 |
| 1 | 2 | Male | 12 OCT. 2004 | 0.349 |
| 2 | 1 | Male | 12 OCT. 2004 | 0.364 |
| 2 | 2 | Male | 12 OCT. 2004 | 0.351 |
| 3 | 1 | Male | 12 OCT. 2004 | 0.360 |
| 3 | 2 | Male | 12 OCT. 2004 | 0.351 |
| 4 | 1 | Male | 12 OCT. 2004 | 0.361 |
| 4 | 2 | Male | 12 OCT. 2004 | 0.367 |
| 5 | 1 | Male | 12 OCT. 2004 | 0.356 |
| 5 | 2 | Male | 12 OCT. 2004 | 0.362 |
| | | | Mean | 0.353 |
| | | | Standard Deviation | 0.015 |
| | | | Maximum | 0.367 |
| | | | Minimum | 0.313 |

TABLE 3

| Test Article | Dose (μg) | Group No. | Animal No. | Time (min) | [Blood Glucose 1] (mg/dL) | [Blood Glucose 2] (mg/dL) | [Blood Glucose Average] (mg/dL) |
|---|---|---|---|---|---|---|---|
| LANTUS insulin glargine | 80 | 1 | 1 | 0 | 95 | 88 | 92 |
| LANTUS insulin glargine | 80 | 1 | 1 | 20 | 88 | 86 | 87 |
| LANTUS insulin glargine | 80 | 1 | 1 | 60 | 48 | 47 | 48 |
| LANTUS insulin qlargine | 80 | 1 | 1 | 120 | 52 | 50 | 51 |
| LANTUS insulin glargine | 80 | 1 | 1 | 180 | 55 | 51 | 53 |
| LANTUS insulin glargine | 80 | 1 | 1 | 240 | 64 | 64 | 64 |
| LANTUS insulin glargine | 80 | 1 | 1 | 480 | 83 | 82 | 83 |
| LANTUS insulin glargine | 80 | 1 | 1 | 720 | 95 | 93 | 94 |
| LANTUS insulin glargine | 80 | 1 | 2 | 0 | 84 | 82 | 83 |
| LANTUS insulin glargine | 80 | 1 | 2 | 20 | 94 | 86 | 90 |
| LANTUS insulin glargine | 80 | 1 | 2 | 60 | 64 | 60 | 62 |
| LANTUS insulin glargine | 80 | 1 | 2 | 120 | 51 | 54 | 53 |
| LANTUS insulin glargine | 80 | 1 | 2 | 180 | 54 | 56 | 55 |
| LANTUS insulin glargine | 80 | 1 | 2 | 240 | 58 | 64 | 61 |
| LANTUS insulin glargine | 80 | 1 | 2 | 480 | 93 | 91 | 92 |
| LANTUS insulin glargine | 80 | 1 | 2 | 720 | 94 | 96 | 95 |
| LANTUS insulin glargine | 160 | 2 | 1 | 0 | 91 | 93 | 92 |
| LANTUS insulin glargine | 160 | 2 | 1 | 20 | 87 | 84 | 86 |
| LANTUS insulin glargine | 160 | 2 | 1 | 60 | 66 | 64 | 65 |
| LANTUS insulin glargine | 160 | 2 | 1 | 120 | 56 | 58 | 57 |
| LANTUS insulin glargine | 160 | 2 | 1 | 180 | 56 | 56 | 56 |
| LANTUS insulin qlargine | 160 | 2 | 1 | 240 | 53 | 52 | 53 |
| LANTUS insulin glargine | 160 | 2 | 1 | 480 | 68 | 67 | 68 |
| LANTUS insulin glargine | 160 | 2 | 1 | 720 | 83 | 82 | 83 |
| LANTUS insulin glargine | 160 | 2 | 2 | 0 | 92 | 90 | 91 |
| LANTUS insulin glargine | 160 | 2 | 2 | 20 | 95 | 92 | 94 |
| LANTUS insulin glargine | 160 | 2 | 2 | 60 | 53 | 56 | 55 |
| LANTUS insulin glargine | 160 | 2 | 2 | 120 | 49 | 47 | 48 |
| LANTUS insulin glargine | 160 | 2 | 2 | 180 | 37 | 42 | 40 |
| LANTUS insulin glargine | 160 | 2 | 2 | 240 | 55 | 52 | 54 |
| LANTUS insulin glargine | 160 | 2 | 2 | 480 | 65 | 70 | 68 |
| LANTUS insulin glargine | 160 | 2 | 2 | 720 | 73 | 69 | 71 |
| LANTUS insulin glargine | 320 | 3 | 1 | 0 | 88 | 91 | 90 |
| LANTUS insulin glargine | 320 | 3 | 1 | 20 | 97 | 102 | 100 |
| LANTUS insulin glargine | 320 | 3 | 1 | 60 | 64 | 62 | 63 |
| LANTUS insulin glargine | 320 | 3 | 1 | 120 | 57 | 55 | 56 |
| LANTUS insulin glargine | 320 | 3 | 1 | 180 | 59 | 56 | 58 |
| LANTUS insulin glargine | 320 | 3 | 1 | 240 | 83 | 84 | 84 |
| LANTUS insulin glargine | 320 | 3 | 1 | 480 | 52 | 54 | 53 |
| LANTUS insulin glargine | 320 | 3 | 1 | 720 | 56 | 55 | 56 |
| LANTUS insulin glargine | 320 | 3 | 2 | 0 | 83 | 88 | 86 |
| LANTUS insulin glargine | 320 | 3 | 2 | 20 | 87 | 89 | 88 |
| LANTUS insulin glargine | 320 | 3 | 2 | 60 | 42 | 41 | 42 |
| LANTUS insulin glargine | 320 | 3 | 2 | 120 | 43 | 46 | 45 |
| LANTUS insulin glargine | 320 | 3 | 2 | 180 | 35 | 33 | 34 |
| LANTUS insulin glargine | 320 | 3 | 2 | 240 | 27 | 23 | 25 |
| LANTUS insulin glargine | 320 | 3 | 2 | 480 | | Not available | |
| LANTUS insulin glargine | 320 | 3 | 2 | 720 | | Not available | |
| LANTUS insulin glargine | 640 | 4 | 1 | 0 | 85 | 82 | 84 |
| LANTUS insulin glargine | 640 | 4 | 1 | 20 | 79 | 82 | 81 |
| LANTUS insulin glargine | 640 | 4 | 1 | 60 | 50 | 46 | 48 |
| LANTUS insulin glargine | 640 | 4 | 1 | 120 | 32 | 33 | 33 |
| LANTUS insulin glargine | 640 | 4 | 1 | 180 | 36 | 37 | 37 |
| LANTUS insulin glargine | 640 | 4 | 1 | 240 | 29 | 32 | 31 |
| LANTUS insulin glargine | 640 | 4 | 1 | 480 | 19 [a] | 19 | 19 |
| LANTUS insulin glargine | 640 | 4 | 1 | 720 | | Not available | |
| LANTUS insulin glargine | 640 | 4 | 2 | 0 | 102 | 101 | 102 |
| LANTUS insulin glargine | 640 | 4 | 2 | 20 | 82 | 83 | 83 |
| LANTUS insulin glargine | 640 | 4 | 2 | 60 | 52 | 52 | 52 |
| LANTUS insulin glargine | 640 | 4 | 2 | 120 | 41 | 38 | 40 |
| LANTUS insulin glargine | 640 | 4 | 2 | 180 | 19 | 20 | 20 |
| LANTUS Insulin glargine | 640 | 4 | 2 | 240 | 19 | 19 | 19 |
| LANTUS insulin glargine | 640 | 4 | 2 | 480 | | Not available | |
| LANTUS insulin glargine | 640 | 4 | 2 | 720 | | Not available | |
| LANTUS insulin glargine | 960 | 5 | 1 | 0 | 87 | 88 | 88 |
| LANTUS insulin glargine | 960 | 5 | 1 | 20 | 61 | 63 | 62 |
| LANTUS insulin glargine | 960 | 5 | 1 | 60 | 34 | 38 | 36 |
| LANTUS insulin glargine | 960 | 5 | 1 | 120 | 21 | 20 | 21 |
| LANTUS insulin glargine | 960 | 5 | 1 | 180 | 19 | 19 | 19 |
| LANTUS insulin glargine | 960 | 5 | 1 | 240 | | Not available | |
| LANTUS insulin glargine | 960 | 5 | 1 | 480 | | Not available | |
| LANTUS insulin glargine | 960 | 5 | 1 | 720 | | Not available | |
| LANTUS insulin glargine | 960 | 5 | 2 | 0 | 92 | 90 | 91 |
| LANTUS insulin glargine | 960 | 5 | 2 | 20 | 72 | 77 | 75 |
| LANTUS insulin glargine | 960 | 5 | 2 | 60 | 37 | 35 | 36 |

TABLE 3-continued

| Test Article | Dose (μg) | Group No. | Animal No. | Time (min) | [Blood Glucose 1] (mg/dL) | [Blood Glucose 2] (mg/dL) | [Blood Glucose Average] (mg/dL) |
|---|---|---|---|---|---|---|---|
| LANTUS insulin glargine | 960 | 5 | 2 | 120 | 27 | 28 | 28 |
| LANTUS insulin glargine | 960 | 5 | 2 | 180 | 19 | 19 | 19 |
| LANTUS insulin glargine | 960 | 5 | 2 | 240 | | Not available | |
| LANTUS insulin glargine | 960 | 5 | 2 | 480 | | Not available | |
| LANTUS insulin glargine | 960 | 5 | 2 | 720 | | Not available | |

[a] Below glucometer measurement range, entered as 19 mg/dL
Animal 3-2 euthanized at 413 min post-dose due to hypoglycemia
Animal 4-1 euthanized at 615 min post-dose due to hypoglycemia
Animal 4-2 euthanized at 244 min post-dose due to hypoglycemia
Animal 5-1 euthanized at 224 min post-dose due to hypoglycemia
Animal 5-2 euthanized at 220 min post-dose due to hypoglycemia Table 4 summarizes selected individual and mean pharmacodynamic parameters for the dose ranging study after insulin glargine was administered by intratracheal instillation to male rats.

TABLE 4

| Group | Animal | Test Article | Dose (μg/animal) | $C_{min}$ (mg/dL) | $T_{min}$ (min) |
|---|---|---|---|---|---|
| 1 | 1 | LANTUS ® Insulin Glargine | 80 | 48 | 60 |
| 1 | 2 | LANTUS ® Insulin Glargine | 80 | 53 | 120 |
| | | Mean | | 50 | 90 |
| | | SD | | 3 | 42 |
| 2 | 1 | LANTUS ® Insulin Glargine | 160 | 53 | 240 |
| 2 | 2 | LANTUS ® Insulin Glargine | 160 | 40 | 180 |
| | | Mean | | 46 | 210 |
| | | SD | | 8 | 42 |
| 3 | 1 | LANTUS ® Insulin Glargine | 320 | 53 | 480 |
| 3 | 2 | LANTUS ® Insulin Glargine | 320 | 25 | 240 |
| | | Mean | | 39 | 360 |
| | | SD | | 16 | 170 |
| 4 | 1 | LANTUS ® Insulin Glargine | 640 | 19[a] | 480 |
| 4 | 2 | LANTUS ® Insulin Glargine | 640 | 19 | 240 |
| | | Mean | | 19 | 360 |
| | | SD | | 0 | 170 |
| 5 | 1 | LANTUS ® Insulin Glargine | 960 | 19 | 180 |
| 5 | 2 | LANTUS ® Insulin Glargine | 960 | 19 | 180 |
| | | Mean | | 19 | 180 |
| | | SD | | 0 | 0 |

Figure 6:
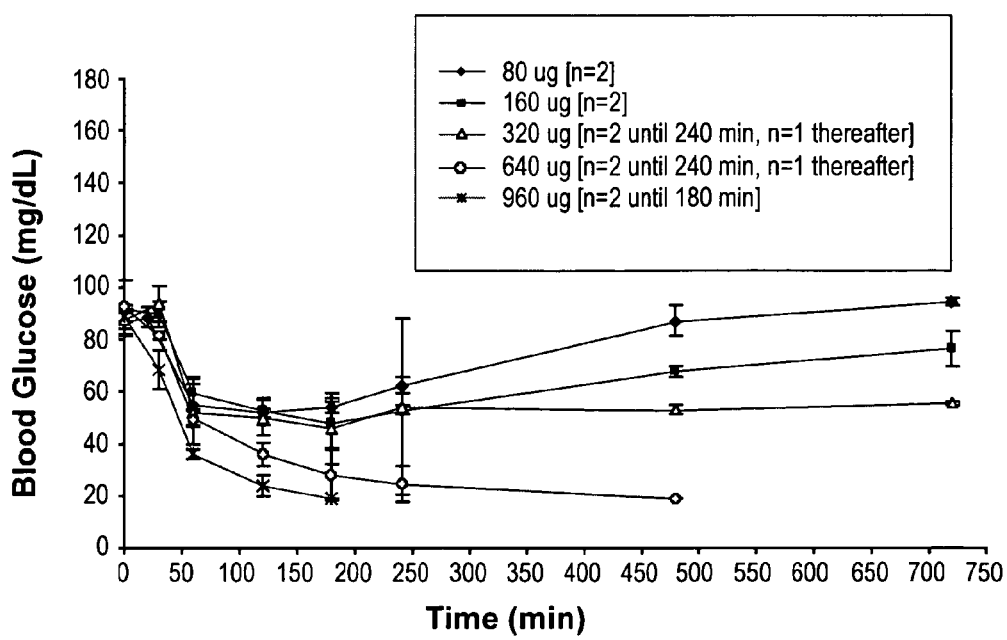
FIG. 6 is a graph showing mean blood glucose concentrations following 80-960 μg intratracheal instillation of insulin glargine to Sprague-Dawley rats. Error bars are standard deviation.

[a] Below glucometer measurement range, entered as 19 mg/dL for calculation of Mean and SD; $C_{min}$ = Minimum blood glucose concentration; $T_{min}$ = Time to $C_{min}$; SD = Standard deviation FIGS. 1-5 show individual blood glucose concentrations following 80-960 μg intratracheal instillation of insulin glargine to Sprague-Dawley rats (n=2). Error bars are standard deviation. FIG. 6 is a graph showing mean blood glucose concentrations following 80-960 μg intratracheal instillation of insulin glargine to Sprague-Dawley rats. Error bars are standard deviation.

Conclusions

In this dose range finding study, 80-320 μg/animal appeared to be a sufficient dose to achieve and occasionally exceed the target glucose suppression (FIG. 6). 640 and 960 μg/animal consistently caused hypoglycemia (<20 mg/dL blood glucose concentration). The 80-320 μg IT doses resulted in the following mean nadir blood glucose levels and times:

| Test Article | Dose (μg/animal) | $C_{min}$ (mg/dL) | $T_{min}$ (min) |
|---|---|---|---|
| LANTUS ® Insulin Glargine | 80 | 50 ± 3 | 90 ± 42 |
| LANTUS ® Insulin Glargine | 160 | 46 ± 8 | 210 ± 42 |
| LANTUS ® Insulin Glargine | 320 | 39 ± 16 | 360 ± 170 |

$C_{min}$ = Minimum blood glucose concentration; $T_{min}$ = Time to $C_{min}$

Mean blood glucose concentrations returned to baseline by 240 and 480 minutes post dose for 80 and 160 μg doses respectively (FIG. 6). Blood glucose levels of Animal 1 at 320 μg dose (Group 3) returned to baseline by 240 minutes then dropped again until 720 minutes post-dose; the cause of this fluctuation is unknown. Animal 2 at 320 μg dose (Group 3), and all Animals at 640 and 960 μg doses (Groups 4 and 5) were euthanized as a result of hypoglycemia.

The optimal IT dose for longer duration of activity appears to be between 160 and 320 μg/animal. A sufficient dose for the definitive study would be 160-240 μg/animal.

Example 2

Pharmacokinetic/Pharmacodynamic Evaluation of Insulin Glargine Following Administration Via Intratracheal Instillation This Example demonstrates the pharmacokinetics/pharmacodynamics (PK/PD) of insulin glargine when administered to rats via intratracheal instillation.

Materials and Methods

LANTUS® insulin glargine (Aventis Pharmaceuticals, Inc., Kansas City, Mo. [lot #40D 058]) is a recombinant human insulin analog which provides a longer duration of activity (up to 24 hours in humans) than that of regular insulin; it differs from human insulin in that the amino acid asparagine at position A21 is replaced by glycine, and two arginines are added to the C-terminus of the B-chain (molecular weight of 6063 Dalton). Insulin glargine has been designed to have low aqueous solubility at neutral pH. At pH 4, as in the LANTUS® injection solution, it is completely soluble. In the neutral pH environment of the subcutaneous site of injection, microprecipitates form from which small amounts of insulin glargine are slowly released resulting in its prolonged activity profile.

Since this PK/PD study evaluated the glucose suppression activity and blood concentration kinetics of insulin glargine when administered by intratracheal (IT) instillation, the acidic solution was not instilled into the lungs as it could have induced injury hence altering PK/PD profile. Instead, the insulin glargine was reformulated for IT administration by preparing an insulin glargine dosing suspension (using the acidic solution) by diluting and adjusting the pH to approximately 7.0.

The test system included 6 pre-cannulated (jugular vein catheter [JVC]) adult male fasted (~17.5 hours) Sprague-Dawley rats (Hilltop Lab Animals, Inc., Scottdale, Pa.). The animals weighed between 0.336-0.362 kg. Prior to dosing, the rats were lightly anesthetized by inhaled Isoflurane (Abbott Laboratories, Chicago, Ill.). Each animal was administered the target dose of the glargine insulin formulation by IT instillation into the lungs. Venous blood samples of approximately 0.4 mL were collected from the JVC at the following time points: predose (~0.33 hours prior to dosing), 0.33, 1, 2, 3, 4, 6, 8, 10, and 12 hours post-dose. Two readings of whole blood glucose concentration (mg/dL) per time point were made using the Glucometer Elite glucose monitor (Bayer Corp., Elkart, Ind.). The remaining portion of the blood sample was processed into plasma and stored at −80° C. for further analysis (data not shown). Pharmacodynamic analysis was performed using Microsoft Office Excel 2003.

Table 5 summarizes the design of the study.

TABLE 5

| Group No. | Control/Test Article | Route of Administration | No. of Animals/Gender | Total Dose of Insulin (μg/animal) | Dose Volume (μL) | No. of Days of Dosing |
| --- | --- | --- | --- | --- | --- | --- |
| 1 | LANTUS ® insulin glargine | IT | 6/M | 160 | 300 | 1 |

Results

Table 6 shows the individual and mean body weights and Table 7 shows individual and mean blood glucose concentrations.

TABLE 6

| Group | Animal | Gender | Date of Birth | Body Weight (kg) |
| --- | --- | --- | --- | --- |
| 1 | 1 | Male | 04 NOV. 2004 | 0.358 |
| 1 | 2 | Male | 04 NOV. 2004 | 0.356 |
| 1 | 3 | Male | 04 NOV. 2004 | 0.353 |
| 1 | 4 | Male | 04 NOV. 2004 | 0.356 |
| 1 | 5 | Male | 04 NOV. 2004 | 0.336 |
| 1 | 6 | Male | 04 NOV. 2004 | 0.362 |
| | | | Mean | 0.354 |
| | | | Standard Deviation | 0.009 |
| | | | Maximum | 0.362 |
| | | | Minimum | 0.336 |

TABLE 7

| Test Formulation | Dose (μg) | Group No. | Animal No. | Time (hr) | [Blood Glucose 1] (mg/dL) | [Blood Glucose 2] (mg/dL) | [Blood Glucose Average] (mg/dL) |
| --- | --- | --- | --- | --- | --- | --- | --- |
| LANTUS insulin glargine | 160 | 1 | 1 | 0 | 92 | 91 | 92 |
| LANTUS insulin glargine | 160 | 1 | 1 | 0.33 | 62 | 64 | 63 |
| LANTUS insulin glargine | 160 | 1 | 1 | 1 | 57 | 58 | 58 |
| LANTUS insulin glargine | 160 | 1 | 1 | 2 | 56 | 55 | 56 |
| LANTUS insulin glargine | 160 | 1 | 1 | 3 | 41 | 40 | 41 |
| LANTUS insulin glargine | 160 | 1 | 1 | 4 | 47 | 52 | 50 |
| LANTUS insulin glargine | 160 | 1 | 1 | 6 | 63 | 64 | 64 |
| LANTUS insulin glargine | 160 | 1 | 1 | 8 | 69 | 70 | 70 |
| LANTUS insulin glargine | 160 | 1 | 1 | 10 | 65 | 75 | 70 |
| LANTUS insulin glargine | 160 | 1 | 1 | 12 | 70 | 71 | 71 |
| LANTUS insulin glargine | 160 | 1 | 2 | 0 | 95 | 92 | 94 |
| LANTUS insulin glargine | 160 | 1 | 2 | 0.33 | 92 | 89 | 91 |
| LANTUS insulin glargine | 160 | 1 | 2 | 1 | 42 | 41 | 42 |
| LANTUS insulin glargine | 160 | 1 | 2 | 2 | 36 | 43 | 40 |
| LANTUS insulin glargine | 160 | 1 | 2 | 3 | 39 | 40 | 40 |
| LANTUS insulin glargine | 160 | 1 | 2 | 4 | 47 | 46 | 47 |
| LANTUS insulin glargine | 160 | 1 | 2 | 6 | 71 | 71 | 71 |
| LANTUS insulin glargine | 160 | 1 | 2 | 8 | 77 | 74 | 76 |

TABLE 7-continued

| Test Formulation | Dose (µg) | Group No. | Animal No. | Time (hr) | [Blood Glucose 1] (mg/dL) | [Blood Glucose 2] (mg/dL) | [Blood Glucose Average] (mg/dL) |
|---|---|---|---|---|---|---|---|
| LANTUS insulin glargine | 160 | 1 | 2 | 10 | 71 | 72 | 72 |
| LANTUS insulin glargine | 160 | 1 | 2 | 12 | 73 | 74 | 74 |
| LANTUS insulin glargine | 160 | 1 | 3 | 0 | 94 | 87 | 91 |
| LANTUS insulin glargine | 160 | 1 | 3 | 0.33 | 81 | 80 | 81 |
| LANTUS insulin glargine | 160 | 1 | 3 | 1 | 55 | 55 | 55 |
| LANTUS insulin glargine | 160 | 1 | 3 | 2 | 56 | 55 | 56 |
| LANTUS insulin glargine | 160 | 1 | 3 | 3 | 61 | 56 | 59 |
| LANTUS insulin glargine | 160 | 1 | 3 | 4 | 64 | 65 | 65 |
| LANTUS insulin glargine | 160 | 1 | 3 | 6 | 75 | 74 | 75 |
| LANTUS insulin glargine | 160 | 1 | 3 | 8 | 80 | 80 | 80 |
| LANTUS insulin glargine | 160 | 1 | 3 | 10 | 79 | 79 | 79 |
| LANTUS insulin glargine | 160 | 1 | 3 | 12 | 84 | 81 | 83 |
| LANTUS insulin glargine | 160 | 1 | 4 | 0 | 99 | 102 | 101 |
| LANTUS insulin glargine | 160 | 1 | 4 | 0.33 | 118 | 120 | 119 |
| LANTUS insulin glargine | 160 | 1 | 4 | 1 | 68 | 70 | 69 |
| LANTUS insulin glargine | 160 | 1 | 4 | 2 | 65 | 63 | 64 |
| LANTUS insulin glargine | 160 | 1 | 4 | 3 | 63 | 63 | 63 |
| LANTUS insulin glargine | 160 | 1 | 4 | 4 | 71 | 68 | 70 |
| LANTUS insulin glargine | 160 | 1 | 4 | 6 | 73 | 75 | 74 |
| LANTUS insulin glargine | 160 | 1 | 4 | 6 | 82 | 73 | 78 |
| LANTUS insulin glargine | 160 | 1 | 4 | 10 | 81 | 80 | 81 |
| LANTUS insulin glargine | 160 | 1 | 4 | 12 | 86 | 83 | 85 |
| LANTUS insulin glargine | 160 | 1 | 5 | 0 | 93 | 93 | 93 |
| LANTUS insulin glargine | 160 | 1 | 5 | 0.33 | 95 | 93 | 94 |
| LANTUS insulin glargine | 160 | 1 | 5 | 1 | 61 | 62 | 62 |
| LANTUS insulin glargine | 160 | 1 | 5 | 2 | 46 | 47 | 47 |
| LANTUS insulin glargine | 160 | 1 | 5 | 3 | 49 | 47 | 48 |
| LANTUS insulin glargine | 160 | 1 | 5 | 4 | 59 | 57 | 58 |
| LANTUS insulin glargine | 160 | 1 | 5 | 6 | 65 | 65 | 65 |
| LANTUS insulin glargine | 160 | 1 | 5 | 8 | 73 | 74 | 74 |
| LANTUS insulin glargine | 160 | 1 | 5 | 10 | 76 | 78 | 77 |
| LANTUS insulin glargine | 160 | 1 | 5 | 12 | 90 | 86 | 88 |
| LANTUS insulin glargine | 160 | 1 | 6 | 0 | 97 | 98 | 98 |
| LANTUS insulin glargine | 160 | 1 | 6 | 0.33 | 107 | 107 | 107 |
| LANTUS insulin glargine | 160 | 1 | 6 | 1 | 56 | 59 | 58 |
| LANTUS insulin glargine | 160 | 1 | 6 | 2 | 44 | 44 | 44 |
| LANTUS insulin glargine | 160 | 1 | 6 | 3 | 42 | 39 | 41 |
| LANTUS insulin glargine | 160 | 1 | 6 | 4 | 53 | 56 | 55 |
| LANTUS insulin glargine | 160 | 1 | 6 | 6 | 70 | 70 | 70 |
| LANTUS insulin glargine | 160 | 1 | 6 | 8 | 79 | 80 | 80 |
| LANTUS insulin glargine | 160 | 1 | 6 | 10 | 66 | 69 | 68 |
| LANTUS insulin glargine | 160 | 1 | 6 | 12 | 89 | 85 | 87 |

Table 8 summarizes selected individual and mean pharmacodynamic parameters for the PK/PD study after administration of reformulated insulin glargine by intratracheal instillation to male rats.

TABLE 8

| Group | Animal | Test Article | Dose (µg/animal) | $C_{min}$ (mg/dL) | $T_{min}$ (hr) |
|---|---|---|---|---|---|
| 1 | 1 | LANTUS ® insulin glargine | 160 | 41 | 3 |
| 1 | 2 | LANTUS ® insulin glargine | 160 | 40 | 2 |
| 1 | 3 | LANTUS ® insulin glargine | 160 | 55 | 1 |
| 1 | 4 | LANTUS ® insulin glargine | 160 | 63 | 3 |
| 1 | 5 | LANTUS ® insulin glargine | 160 | 47 | 2 |
| 1 | 6 | LANTUS ® insulin glargine | 160 | 41 | 3 |
| | | Mean | | 48 | 2.3 |
| | | SD | | 16 | 0.4 |

Figure 7:
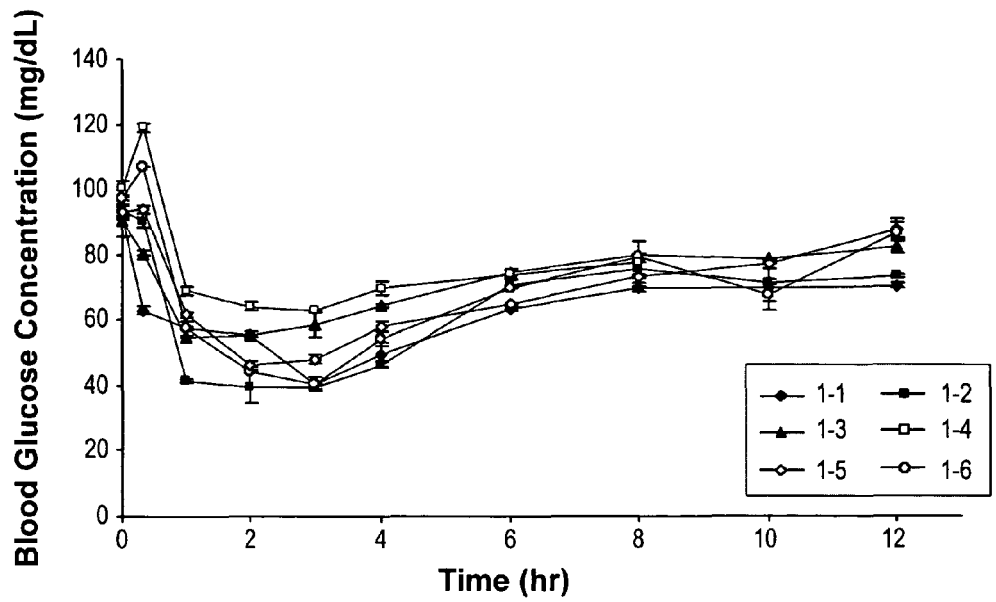
FIG. 7 is a graph showing individual blood glucose concentrations following 160 μg intratracheal instillation of reformulated insulin glargine to Sprague-Dawley rats (n=6). Error bars show standard deviation.
Figure 8:
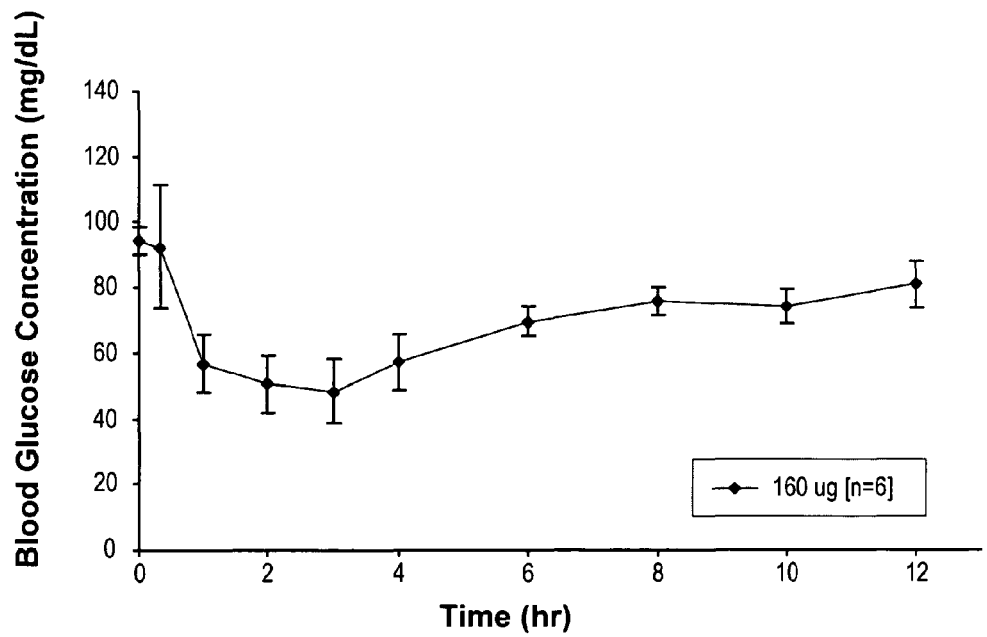
FIG. 8 is a graph showing mean blood glucose concentrations following 160 μg intratracheal instillation of reformulated insulin glargine to Sprague-Dawley rats. Error bars show standard deviation.

$C_{min}$ = Minimum blood glucose concentration; $T_{min}$ = Time to $C_{min}$; SD = Standard deviation FIG. 7 is a graph showing individual blood glucose concentrations following 160 µg intratracheal instillation of reformulated insulin glargine to Sprague-Dawley rats (n=6). FIG. 8 is a graph showing mean blood glucose concentrations following 160 µg intratracheal instillation of reformulated insulin glargine to Sprague-Dawley rats.

Conclusions

The 160-µg dose selected for this definitive PK/PD study, determined from Example 1, above, resulted in average nadir blood glucose levels of 48±16 g/dL at 2.3±0.4 hours post dose (Table 8). As seen in FIG. 8, mean blood glucose concentrations were suppressed at target levels of 40-60 mg/dL until 4 hours post dose with an onset of action at about 1 hour.

Example 3

Preparation of 20% and 90% Glargine Insulin Formulations

Glargine insulin formulations were prepared having the following components, listed in Table 9.

TABLE 9

| | Solid Percent | |
| --- | --- | --- |
| | 20% formulation | 90% formulation |
| Insulin Glargine | 20 | 90 |
| Leucine | 70 | 8.75 |
| Trehalose | 10 | 1.25 |
| $ZnCl_2$ | 0.15 | 0.67 |
| Sodium Citrate | 0.08 | 0.09 |

$[Zn]:[Glargine]_6 = 2:1$

Table 9 shows the solid contents of the 20% and 90% insulin glargine formulations. Briefly, solutions were prepared having the components listed above, at a solids concentration in the solution of 1%. The solutions were formed by mixing stock solutions, as follows:

| 20% formulation | |
| --- | --- |
| | Volume from various stock solutions |
| Glargine stock: 3.48 mg/ml in 0.05 mM citric acid. | 17.5 ml |
| Trehalose/Leucine stock: 2.86 mg/ml/20 mg/ml in water | 10.5 ml |
| ZnCl2 stock 0.225 mg/ml in water | 2.0 ml |

The insulin glargine was purified from LANTUS. For the 20% insulin glargine formulation, insulin glargine was first purified from LANTUS using a PD10 desalting column, then concentrated by an Amicon Ultra-15 centrifugal filter device with molecular weight cutoff 5000. Finally the concentrated glargine solution was diluted to 3.48 mg/ml using 0.05 mM citric buffer (pH 4).

| 90% formulation | |
| --- | --- |
| | Volume from various stock solutions |
| Glargine stock: 24.88 mg/ml in 0.05 mM citric acid. | 9.65 ml |
| Trehalose/Leucine stock: 2.86 mg/ml/20 mg/ml in water | 1.17 ml |
| ZnCl2 stock 0.225 mg/ml in water | 8.00 ml |
| Citric buffer 0.05 mM | 7.89 ml |

Like the 20% formulation, the insulin glargine was purified from LANTUS. Insulin glargine was desalted and concentrated by an Amicon Ultra-15 centrifugal filter device with molecular weight cutoff 5000 (without using a PD10 desalting column). The final concentration of glargine was 24.88 mg/ml.

Both formulations were spray-dried using Buchi Mini Spray Dryer B-191. For both formulations, the solid content of the feeding solutions was 10 mg/ml and the solution feeding rate was 4 ml/min. For The 20% formulation, the inlet and outlet temperatures were 85° C. and 55° C. respectively. For the 90% formulation, the inlet and outlet temperatures were 90° C. and 60° C. respectively. The powder yield was 60.9% for 20% formulation and 50.6% for 90% formulation.

Example 4

Chemical Stability Testing of 20% and 90% Glargine Insulin Formulations

Chemical stability for 4 months and 6.5 months storage of the 20% insulin glargine formulation and for 2 months storage of the 90% insulin glargine formulation were tested.

Figure 9:
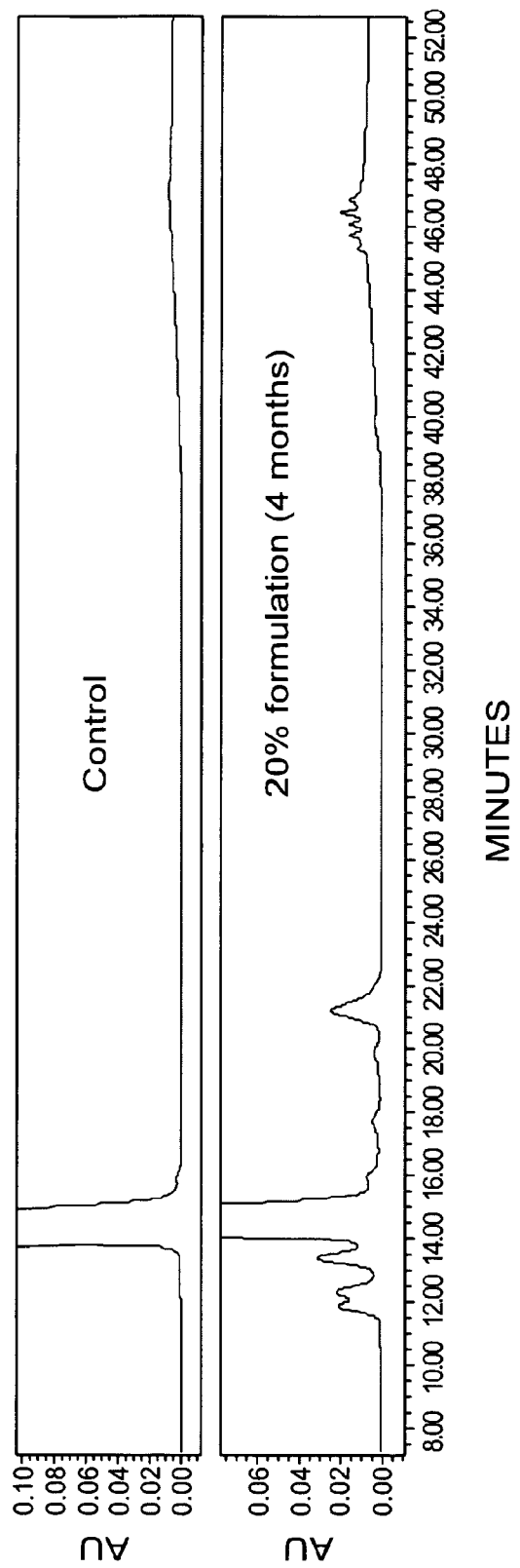
FIG. 9 shows a typical HPLC chromatograph of an insulin glargine formulation of the present invention, obtained after an aging test, in comparison with a control.
Figure 10:
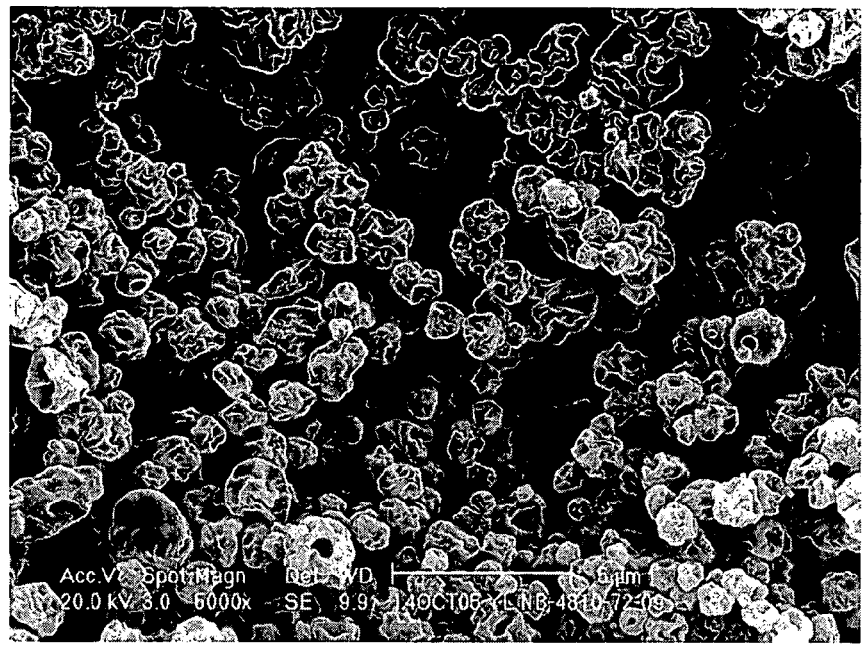
FIG. 10 is an electron micrograph of a 20% insulin glargine formulation according to the invention (after 4 months aging), at 5 μm resolution.
Figure 11:
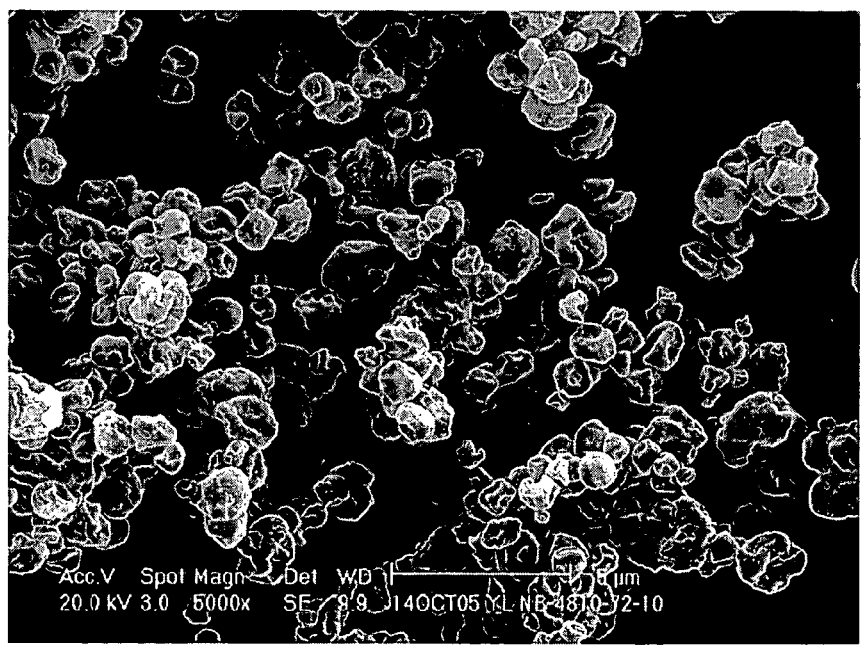
FIG. 11 is an electron micrograph of a 90% insulin glargine formulation according to the invention (time=0), at 5 μm resolution.
Figure 12:
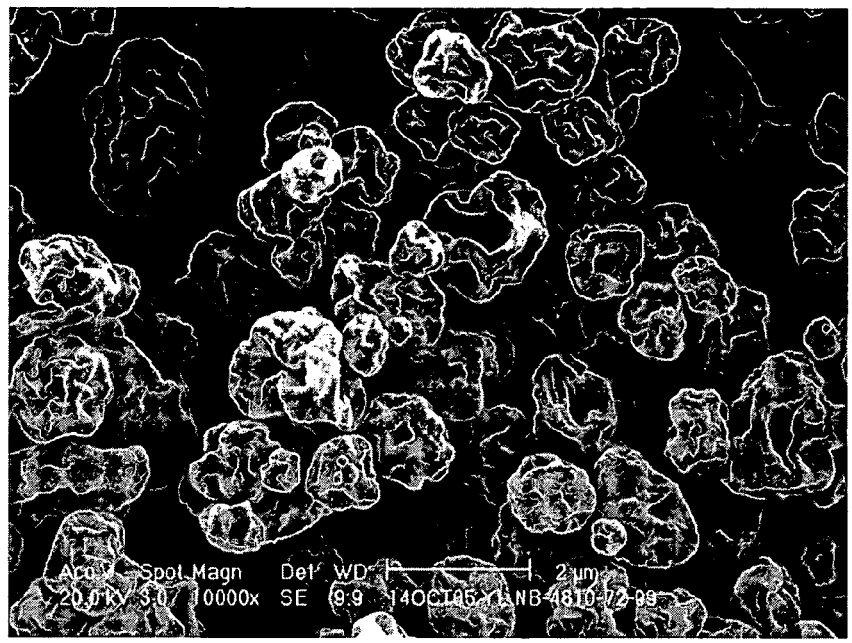
FIG. 12 is an electron micrograph of a 20% insulin glargine formulation according to the invention (after 4 months aging), at 2 μm resolution.
Figure 13:
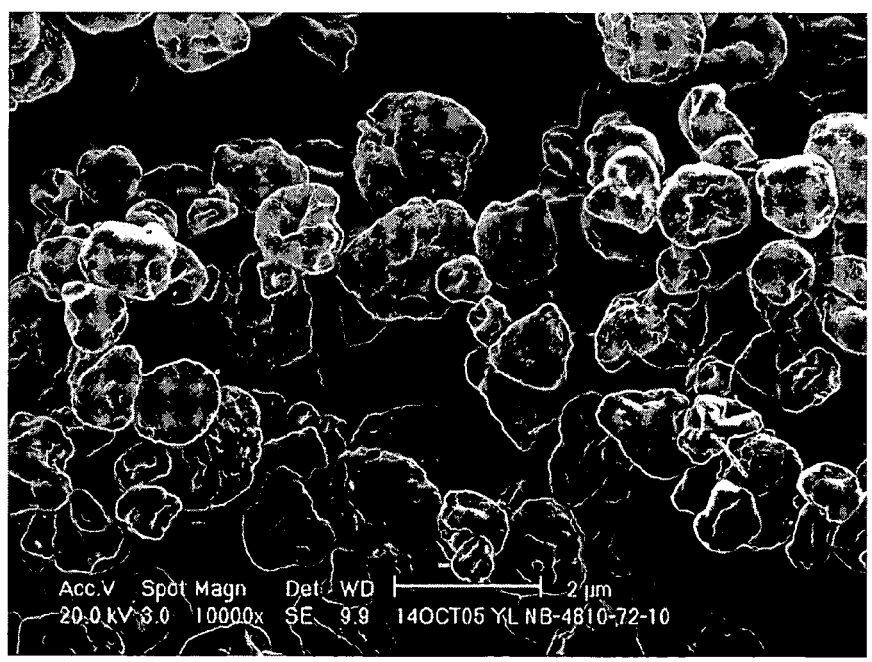
FIG. 13 is an electron micrograph of a 90% insulin glargine formulation according to the invention (time=0), at 2 μm resolution.
Figure 14:
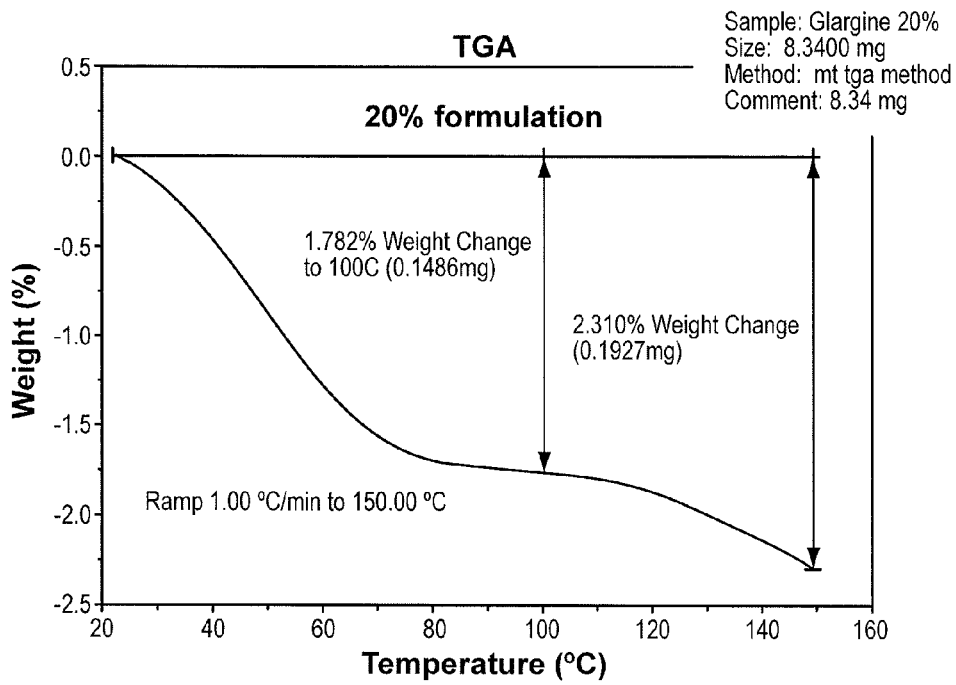
FIG. 14 shows a graph of a thermogravimetric analysis of a 20% insulin glargine formulation according to the invention.
Figure 15:
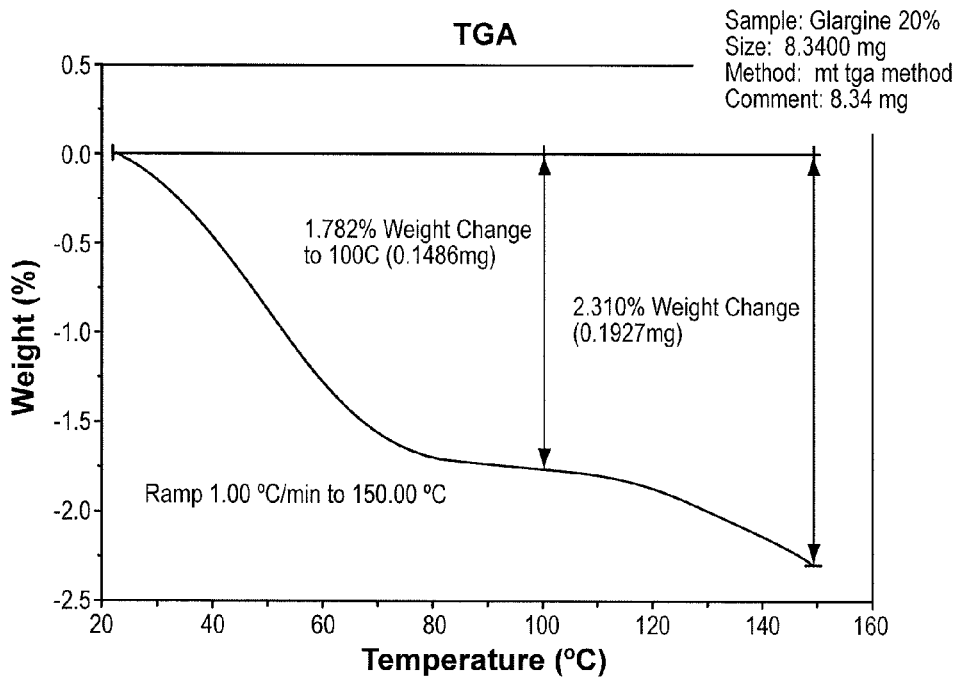
FIG. 15 shows a graph of a thermogravimetric analysis of a 90% insulin glargine formulation according to the invention.
Figure 16:
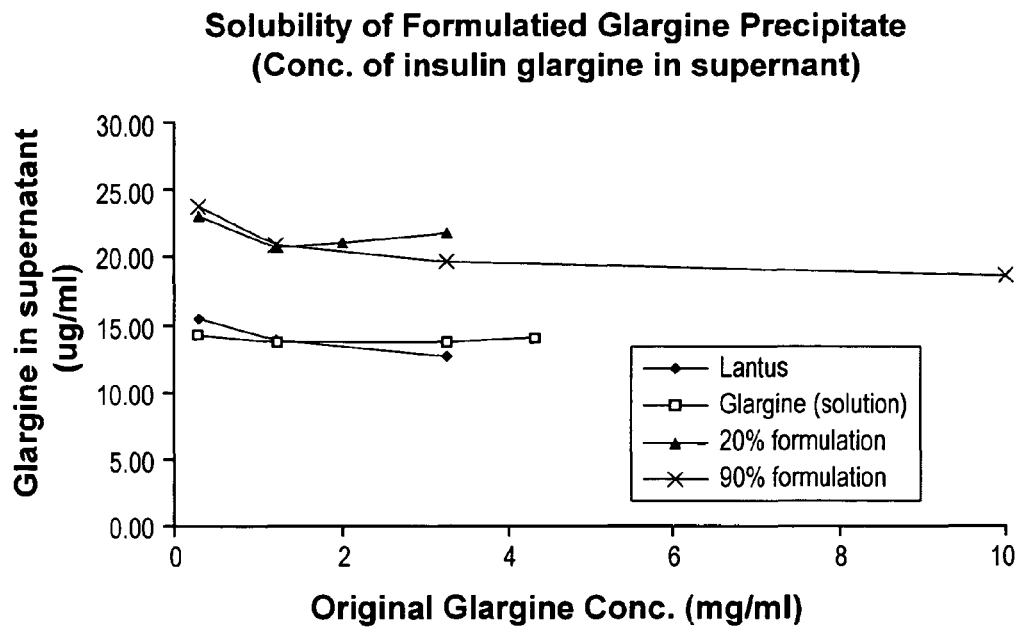
FIG. 16 shows a graph of insulin glargine concentrations in supernatant after precipitation.
Figure 17:
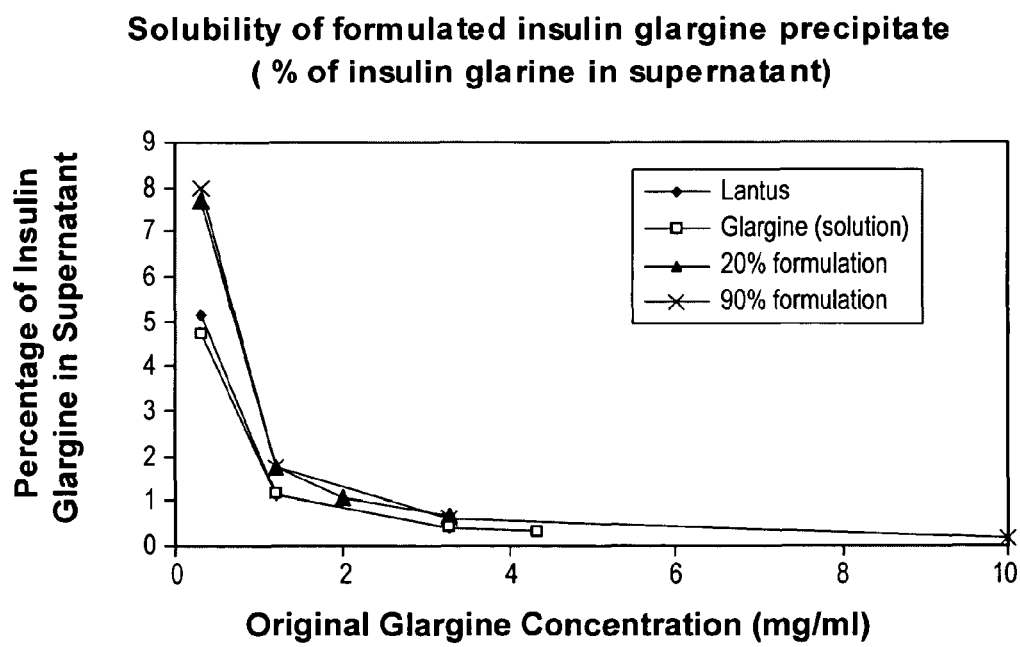
FIG. 17 shows a graph of percent of insulin glargine in supernatant after precipitation.

Briefly, the formulated dry powder was filled in blisters and stored in ambient dry box storage. At the test time, the formulations were dissolved to a concentration of 1.0 mg/ml in water. Reverse phase HPLC was used to analyze the degradation of the insulin glargine. Insulin glargine content and HMWP (high molecular weight protein) content were monitored. LANTUS™ was used as a control. FIG. 9 shows a typical chromatograph of the sample and control.

Table 10 summarizes the stability study results. After 4 months storage, the 20% formulation in blister showed degradation of the main peak and appearance of the HMWP. However, there was little further main peak degradation after another 2.5 months of storage. The 20% formulation also showed visible caking after 6.5 months storage, indicating the solid-state stability of the excipients. The spray-dried bulk powder showed minimal main peak degradation and very little HMWP. The 90% formulation in blister showed some main peak degradation after 2 months storage, but was more stable than the 20% formulation.

TABLE 10

| Time | Formulation | Glargine (%) | HMWP (%) |
| --- | --- | --- | --- |
| T = 0 | Lantus | 99.6 | 0.020 |
| T = 4 months | 20% blister | 90.5 | 1.4 |
| T = 6.5 months | 20% blister | 89.0 | 1.3 |
| T = 0 | 90% bulk | 99.7 | 0.14 |
| T = 2 months | 90% bulk | 99.2 | 0.20 |
| T = 2 months | 90% blister | 96.8 | 1.3 |

Example 5

Aerosol Performance of the 20% and 90% Glargine Insulin Formulations

Aerosol performance was measured by using a Pulmonary Delivery System (PDS), as disclosed in U.S. Pat. No. 6,257,233, which is incorporated by reference herein in its entirety, connected to an Andersen Cascade Impactor under the conditions shown in Table 11, below. Table 11 also shows the aerosol testing results of the 20% formulation after 4 months storage, and the results of the 90% formulation after 1.5 months storage. It shows that both formulations had good aerosol performance.

TABLE 11

| Summary of Emitted Dose using the PDS at 30 LPM | | | | | |
|---|---|---|---|---|---|
| Formulation | Fill Weight (mg) | % ED | ED SD | % Left | % Left SD |
| 20%[1] | 3.5 | 69 | 3 | 11 | 3 |
| 90%[2] | 3.5 | 68 | 6 | 8 | 3 |

TABLE 11-continued

Summary of PSD using the PDS at 28.3 LPM

| Formulation | Fill Weight (mg) | % Recovery | MMAD | % FPD <4.7 mm | % FPD <3.3 mm |
|---|---|---|---|---|---|
| 20% | 3.5 | 64 | 2.7 | 61 | 45 |
| 90% | 3.5 | 66 | 2.8 | 61 | 43 |

[1] n = 5,
[2] n = 3
Andersen Cascade Impactor with coated plates n = 1

Example 6

Particle Morphology of the 20% and 90% Glargine Insulin Formulations

FIGS. 10 to 13 are SEM (Scanning Electron Microscopy) results for insulin glargine formulations. The 20% formulation is more wrinkled than the 90% formulation. Both formulations are high dispersible with a PDS device, as demonstrated in Table 11.

Example 7

Volatile Contents of the 20% and 90% Glargine Insulin Formulations

TGA (Thermogravimetric Analysis) was used to measure the volatile content in the insulin glargine formulations. The volatile contents were 1.782% for the 20% formulation and 6.275% for the 90% formulation when the temperature changed up to 100° C. FIGS. 14 and 15 show the results.

Example 8

Solubility of the 20% and 90% Glargine Insulin Formulations

The insulin glargine formulations were reconstituted in water and made into various concentrations, as indicated in Table 12 below, as original glargine concentrations. Phosphate buffer (200 mM, pH 7.4) was then added to the solutions to a final phosphate concentration of 20 mM. Insulin glargine was precipitated in the neutralized solution. The insulin glargine concentration in the supernatant was then analyzed by reverse phase HPLC. The result is shown in Table 12 as well as in FIG. 16 and FIG. 17.

TABLE 12

| Samples | Orignal Glargine Conc. (mg/ml) | Glargine Conc. in supernatant (ug/ml) | Percentage of glargine in supernatant (%) |
|---|---|---|---|
| LANTUS 0.3 | 0.3 | 15.47 | 5.2 |
| LANTUS 1.2 | 1.2 | 13.79 | 1.1 |
| LANTUS 3.27 | 3.27 | 12.59 | 0.4 |
| Glargine 0.3 | 0.3 | 14.27 | 4.8 |
| Glargine 1.2 | 1.2 | 13.65 | 1.1 |
| Glargine 3.27 | 3.27 | 13.72 | 0.4 |
| Glargine 4.35 | 4.35 | 14.04 | 0.3 |
| Glar 20% 0.3 | 0.3 | 23.06 | 7.7 |
| Glar 20% 1.2 | 1.2 | 20.81 | 1.7 |
| Glar 20% 2.0 | 2 | 21.18 | 1.1 |
| Glar 20% 3.27 | 3.27 | 21.82 | 0.7 |
| Glar 90% 0.3 | 0.3 | 23.86 | 8.0 |
| Glar 90% 1.2 | 1.2 | 21.03 | 1.8 |
| Glar 90% 3.27 | 3.27 | 19.72 | 0.6 |
| Glar 90% 10.0 | 10 | 18.63 | 0.2 |

The trend showed that the higher the concentration of the original insulin glargine, the lower the solubility of the precipitate it formed when reconstituted in neutral buffer.

Although the present invention has been described in considerable detail with regard to certain versions thereof, other versions are possible, and alterations, permutations and equivalents of the version shown will become apparent to those skilled in the art upon a reading of the specification and study of the drawings. Also, the various features of the versions herein can be combined in various ways to provide additional versions of the present invention. Furthermore, certain terminology has been used for the purposes of descriptive clarity, and not to limit the present invention. Therefore, any appended claims should not be limited to the description of the preferred versions contained herein and should include all such alterations, permutations, and equivalents as fall within the true spirit and scope of the present invention.

Having now fully described this invention, it will be understood to those of ordinary skill in the art that the methods of the present invention can be carried out with a wide and equivalent range of conditions, formulations, and other parameters without departing from the scope of the invention or any embodiments thereof.

All patents and publications cited herein are hereby fully incorporated by reference in their entirety. The citation of any publication is for its disclosure prior to the filing date and should not be construed as an admission that such publication is prior art or that the present invention is not entitled to antedate such publication by virtue of prior invention. Furthermore, it is noted that U.S. patent application entitled "SUSTAINED RELEASE FORMULATIONS FOR PULMONARY DELIVERY" by Stelios Tzannis and filed the same day as the present application is hereby fully incorporated by reference in its entirety.

What is claimed is:

1. An aerosolized formulation, comprising:

a first insulin derivative having an isoelectric point (p1) ranging from about 6.5 to about 7.5, wherein the first insulin derivative is glargine insulin;

a second insulin or insulin derivative;

Trehalose;

Leucine;

a liquid carrier, which is water, ethanol, ethanol-water, or saline; and a precipitating agent, which is a free cation selected from at least one of zinc, copper, cobalt, iron, manganese, vanadium, cadmium, magnesium, calcium, and barium;

wherein the first insulin derivative and the precipitating agent are dissolved in the liquid carrier;

wherein the molar ratio of the precipitating agent to the first insulin derivative is from about 1:3 to about 5:1;

wherein the first insulin derivative is present in an amount of from about 20 weight % to about 99 weight %.

2. The aerosolized formulation of claim 1, wherein the molar ratio of the precipitating agent to the first insulin derivative is about 5:3.

3. The aerosolized formulation of claim 1, wherein the second insulin or insulin derivative has a different isoelectric point than that of the first insulin derivative.

* * * * *